US012667640B2

(12) United States Patent (10) Patent No.: US 12,667,640 B2

Wen et al. (45) Date of Patent: Jun. 30, 2026

(54) AIR CONDITIONER INDOOR UNIT, AIR CONDITIONER, AND PURIFICATION CONTROL METHOD OF AIR CONDITIONER INDOOR UNIT

(71) Applicant: HISENSE AIR CONDITIONING CO., LTD., Qingdao (CN)

(72) Inventors: Bo Wen, Qingdao (CN); Yunxi Li, Qingdao (CN); Lingqing Ma, Qingdao (CN); Fengjiao Zhang, Qingdao (CN); Xinyu Zhang, Qingdao (CN)

(73) Assignee: HISENSE AIR CONDITIONING CO., LTD., Qingdao (CN)

( * ) Notice: Subject to any disclaimer, the term of this patent is extended or adjusted under 35 U.S.C. 154(b) by 397 days.

(21) Appl. No.: 18/355,248

(22) Filed: Jul. 19, 2023

(65) Prior Publication Data

US 2024/0016969 A1 Jan. 18, 2024

Related U.S. Application Data

(63) Continuation of application No. PCT/CN2022/090644, filed on Apr. 29, 2022.

(30) Foreign Application Priority Data

May 18, 2021 (CN) .......................... 202110539736.6
Jun. 24, 2021 (CN) .......................... 202121429500.9

(51) Int. Cl.
*F24F 8/30* (2021.01)
*A61L 9/22* (2006.01)
(Continued)

(52) U.S. Cl.
CPC .................. *A61L 9/22* (2013.01); *F24F 8/30* (2021.01); *F24F 11/65* (2018.01);
(Continued)

(58) Field of Classification Search
CPC ..................................... A61L 9/22; F24F 8/30
See application file for complete search history.

(56) References Cited

U.S. PATENT DOCUMENTS

2004/0007000 A1* 1/2004 Takeda .................... F24F 8/192
62/264
2006/0233660 A1* 10/2006 Furuhashi ................ F24F 11/56
422/28

(Continued)

FOREIGN PATENT DOCUMENTS

CN 201811356 U 4/2011
CN 103135513 A 6/2013
(Continued)

OTHER PUBLICATIONS

International Search Report and Written Opinion dated Jul. 27, 2022 in corresponding International Application No. PCT/CN2022/090644, translated, 17 pages.

(Continued)

*Primary Examiner* — Kevin Joyner
(74) *Attorney, Agent, or Firm* — MH2 Technology Law Group LLP

(57) ABSTRACT

An air conditioner indoor unit includes a power supply device, a control device, a negative electrode discharge device, and a positive electrode discharge device. The negative electrode discharge device is configured to ionize air to generate air negative ions. The positive electrode discharge device is configured to ionize air to generate air positive ions. The control device is configured to determine an operation mode of the air conditioner indoor unit according to first information, control the power supply device to supply power to the negative electrode discharge device and the positive electrode discharge device in a case where the operation mode is a first purification mode, and control the power supply device to supply power to the negative elec- (Continued)

20 trode discharge device and stop supplying power to the positive electrode discharge device in a case where the operation mode is a second purification mode.

19 Claims, 10 Drawing Sheets

(51) Int. Cl.
*F24F 11/65* (2018.01)
*F24F 120/10* (2018.01)

(52) U.S. Cl.
CPC ...... *A61L 2209/111* (2013.01); *A61L 2209/16* (2013.01); *F24F 2120/10* (2018.01)

(56) References Cited

U.S. PATENT DOCUMENTS

| | | | |
|---|---|---|---|
| 2015/0352564 A1 | 12/2015 | Genereux et al. | |
| 2016/0310628 A1 | 10/2016 | Jiang et al. | |
| 2023/0119625 A1* | 4/2023 | Chunduri | H05H 1/48 422/4 |

FOREIGN PATENT DOCUMENTS

| | | | |
|---|---|---|---|
| CN | 107449073 A | 12/2017 | |
| CN | 108448383 A | 8/2018 | |
| CN | 112178866 A | 1/2021 | |
| CN | 112283865 A | 1/2021 | |
| CN | 112377990 A | 2/2021 | |
| CN | 112484245 A | 3/2021 | |
| CN | 112747423 A | 5/2021 | |
| CN | 215260174 U | 12/2021 | |
| CN | 215723963 U | 2/2022 | |
| JP | 2017519611 A | 7/2017 | |
| KR | 102191144 B1 | 12/2020 | |

OTHER PUBLICATIONS

Chinese First Office Action dated Mar. 31, 2022 in corresponding Chinese Application No. 202110539736.6, translated, 19 pages.
Chinese Second Office Action dated Nov. 1, 2022 in corresponding Chinese Application No. 202110539736.6, translated, 11 pages.
"Integration Technology of Eco-Function Elementary Meterials and Composite Buildings Materials," Oct. 31, 2008, translated, 6 pages.

* cited by examiner

Start

Detect whether there are people in environment space

No

Yes

Operate in a first purification mode or a second purification mode

Pause or stop operating in the first purification mode or the second purification mode

AIR CONDITIONER INDOOR UNIT, AIR CONDITIONER, AND PURIFICATION CONTROL METHOD OF AIR CONDITIONER INDOOR UNIT

CROSS-REFERENCE TO RELATED APPLICATIONS

This application is a continuation application of International Patent Application No. PCT/CN2022/090644, filed on Apr. 29, 2022, which claims priority to Chinese Patent Application No. 202110539736.6, filed on May 18, 2021, and Chinese Patent Application No. 202121429500.9, filed on Jun. 24, 2021, which are incorporated herein by reference in their entireties.

TECHNICAL FIELD

The present disclosure relates to the technical field of air conditioning, and in particular, to an air conditioner indoor unit, an air conditioner, and a purification control method of an air conditioner indoor unit.

BACKGROUND

Viruses, bacteria, fungi, and other microorganisms may spread in the air, which causes microbial contamination of the air and affects human health. In order to efficiently kill harmful microorganisms in the indoor environment and keep the indoor air environment healthy, some air conditioners are equipped with ion generating apparatuses to achieve a purpose of sterilization and disinfection.

SUMMARY

In an aspect, an air conditioner indoor unit is provided. An operation mode of the air conditioner indoor unit includes a first purification mode and a second purification mode, and the air conditioner indoor unit includes a power supply device, a control device, a negative electrode discharge device, and a positive electrode discharge device. The negative electrode discharge device is coupled to the power supply device and configured to discharge in the first purification mode or the second purification mode to ionize air to generate air negative ions. The positive electrode discharge device is coupled to the power supply device and configured to discharge in the first purification mode to ionize air to generate air positive ions. The air positive ions are cooperated with the air negative ions generated by the negative electrode discharge device to perform disinfection and sterilization. The control device is configured to determine the operation mode of the air conditioner indoor unit according to first information, control the power supply device to supply power to the negative electrode discharge device and the positive electrode discharge device in a case where the operation mode of the air conditioner indoor unit is the first purification mode, and control the power supply device to supply power to the negative electrode discharge device and stop supplying power to the positive electrode discharge device in a case where the operation mode of the air conditioner indoor unit is the second purification mode. The first information includes at least one of a purification mode trigger instruction, environment information, or operating duration information.

In another aspect, an air conditioner is provided. The air conditioner includes the air conditioner indoor unit as described in any of the above embodiments and an air conditioner outdoor unit. The air conditioner outdoor unit is connected with the air conditioner indoor unit.

In yet another aspect, a purification control method of an air conditioner indoor unit is provided. An operation mode of the air conditioner indoor unit includes a first purification mode and a second purification mode, and the air conditioner indoor unit includes a positive electrode discharge device and a negative electrode discharge device. When the air conditioner indoor unit operates in the first purification mode, the positive electrode discharge device and the negative electrode discharge device operate; and when the air conditioner indoor unit operates in the second purification mode, the negative electrode discharge device operates. The purification control method includes: detecting, by the air conditioner indoor unit, whether there are people in environment space; operating, by the air conditioner indoor unit, in the first purification mode or the second purification mode when detecting there are no people in the environment space; and pausing or stopping operating, by the air conditioner indoor unit, in the first purification mode or the second purification mode when detecting there are people in the environment space.

DETAILED DESCRIPTION

Figure 1:
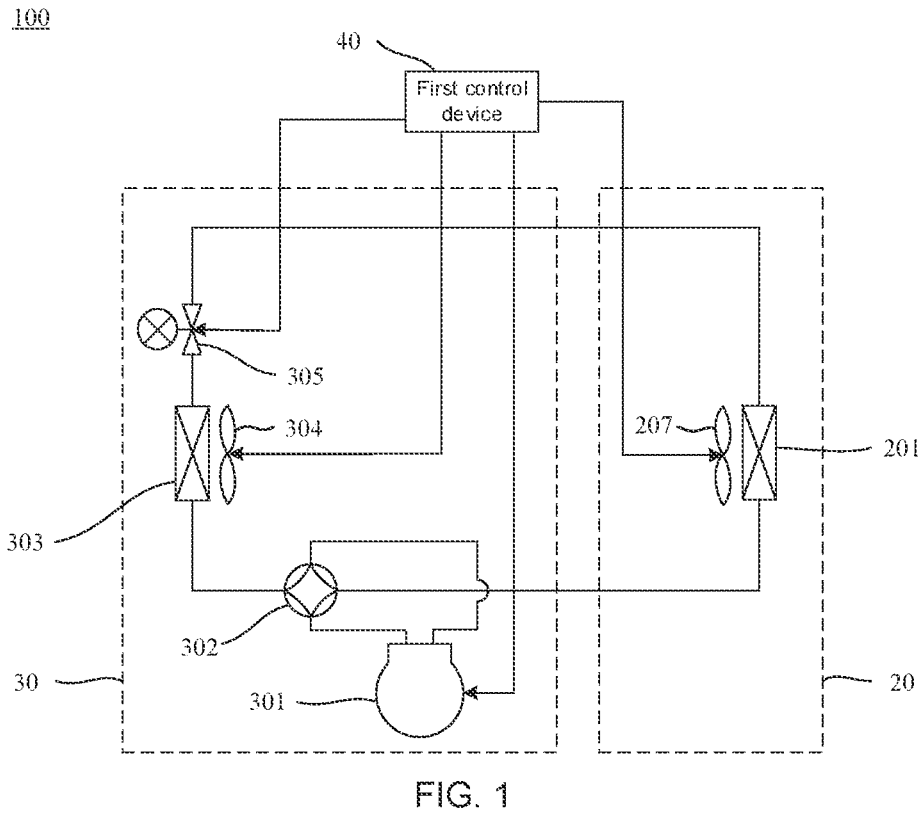
FIG. 1 is a schematic diagram of an air conditioner, in accordance with some embodiments.

Some embodiments of the present disclosure will be described clearly and completely with reference to the accompanying drawings below. Obviously, the described embodiments are merely some but not all of embodiments of the present disclosure. All other embodiments obtained by a person having ordinary skill in the art based on embodiments of the present disclosure shall be included in the protection scope of the present disclosure.

Unless the context requires otherwise, throughout the specification and the claims, the term "comprise" and other forms thereof such as the third-person singular form "comprises" and the present participle form "comprising" are construed as an open and inclusive meaning, i.e., "including, but not limited to." In the description of the specification, the terms such as "one embodiment," "some embodiments," "exemplary embodiments," "example," "specific example," or "some examples" are intended to indicate that specific features, structures, materials, or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics described herein may be included in any one or more embodiments or examples in any suitable manner.

Hereinafter, the terms "first" and "second" are only used for descriptive purposes, and cannot be construed as indicating or implying the relative importance or implicitly indicating the number of indicated technical features. Thus, features defined with "first" and "second" may explicitly or implicitly include one or more of the features. In the description of the embodiments of the present disclosure, the terms "a plurality of" and "the plurality of" each mean two or more unless otherwise specified.

In the description of some embodiments, the expressions "coupled" and "connected" and their derivatives may be used. For example, the term "connected" may be used in the description of some embodiments to indicate that two or more components are in direct physical or electrical contact with each other. For another example, the term "coupled" may be used in the description of some embodiments to indicate that two or more components are in direct physical or electrical contact. However, the term "coupled" or "communicatively coupled" may also mean that two or more components are not in direct contact with each other but still cooperate or interact with each other. The embodiments disclosed herein are not necessarily limited to the content herein.

The phrase "at least one of A, B, and C" has the same meaning as the phrase "at least one of A, B, or C," and they both include the following combinations of A, B, and C: only A, only B, only C, a combination of A and B, a combination of A and C, a combination of B and C, and a combination of A, B, and C.

The phrase "A and/or B" includes the following three combinations: only A, only B, and a combination of A and B.

The use of "applicable to" or "configured to" herein indicates an open and inclusive expression, which does not exclude devices that are applicable to or configured to perform additional tasks or steps.

In addition, the use of the phrase "based on" has an open and inclusive meaning, since a process, step, calculation, or other action that is "based on" one or more of the stated conditions or values may, in practice, be based on additional conditions or values exceeding those stated.

Particulate matter is one of the important components of air pollutants. Since the particulate matter has extremely small particle size, it may be suspended and retained in the air for a long time. Therefore, when human breathes, the particulate matter will enter the respiratory tract, which leads to lung inflammation and causes damage to lung function.

Viruses, bacteria, fungi, and other microorganisms may also spread in the air, which causes microbial contamination of the air and affects human health.

In order to remove particulate matter and harmful microorganisms in the indoor environment and keep the indoor air environment healthy, an air conditioner is usually equipped with an ion generating apparatus. The ion generating apparatus may generate positive ions or negative ions, these ions may adsorb particulate matter by static electricity, and the combination of positive ions and negative ions may kill harmful microorganisms.

However, the positive ions and the negative ions are also harmful to the human body to a certain extent. Therefore, if a purification control method of the air conditioner is unreasonable, it may not only fail to effectively kill the harmful microorganisms and remove the particulate matter in the environment space, but also cause certain damage to the human body.

Some embodiments of the present disclosure provide an air conditioner.

FIG. 1 is a schematic diagram of an air conditioner, in accordance with some embodiments.

As shown in FIG. 1, the air conditioner 100 includes an air conditioner indoor unit 20, an air conditioner outdoor unit 30, and an expansion valve 305. The air conditioner indoor unit 20 and the air conditioner outdoor unit 30 are connected by a pipe to convey a refrigerant. The air conditioner indoor unit 20 includes an indoor heat exchanger 201 and an indoor fan 207. The air conditioner outdoor unit 30 includes a compressor 301, a four-way valve 302, an outdoor heat exchanger 303, and an outdoor fan 304. The compressor 301, the outdoor heat exchanger 303, the expansion valve 305, and the indoor heat exchanger 201 that are connected in sequence form a refrigerant loop. The refrigerant circulates in the refrigerant loop and exchanges heat with air through the outdoor heat exchanger 303 and the indoor heat exchanger 201, so as to implement a cooling mode or a heating mode of the air conditioner 100.

The compressor 301 is configured to compress the refrigerant, so that a low-pressure refrigerant is compressed to be a high-pressure refrigerant.

The outdoor heat exchanger 303 is configured to perform heat-exchange between outdoor air and the refrigerant conveyed in the outdoor heat exchanger 303. For example, the outdoor heat exchanger 303 operates as a condenser in the cooling mode of the air conditioner 100, so that the refrigerant compressed by the compressor 301 dissipates heat into the outdoor air through the outdoor heat exchanger 303 to be condensed; and the outdoor heat exchanger 303 operates as an evaporator in the heating mode of the air conditioner 100, so that the decompressed refrigerant absorbs heat from the outdoor air through the outdoor heat exchanger 303 to be evaporated.

In some embodiments, the outdoor heat exchanger 303 further includes heat-exchange fins, so as to expand a contact area between the outdoor air and the refrigerant conveyed in the outdoor heat exchanger 303, thereby improving heat-exchange efficiency between the outdoor air and the refrigerant.

The outdoor fan 304 is configured to suck the outdoor air into the air conditioner outdoor unit 30 through an outdoor air inlet of the air conditioner outdoor unit 30, and send the outdoor air, after heat-exchange between the outdoor air and the outdoor heat exchanger 303, out through an outdoor air outlet of the air conditioner outdoor unit 30. The outdoor fan 304 provides power for the flow of the outdoor air.

The expansion valve 305 is connected between the outdoor heat exchanger 303 and the indoor heat exchanger 201. The pressure of the refrigerant flowing between the outdoor heat exchanger 303 and the indoor heat exchanger 201 is adjusted by an opening degree of the expansion valve 305, so as to adjust the flow of the refrigerant flowing between the outdoor heat exchanger 303 and the indoor heat exchanger 201. The flow and the pressure of the refrigerant flowing between the outdoor heat exchanger 303 and the indoor heat exchanger 201 will affect the heat-exchange performance of the outdoor heat exchanger 303 and the indoor heat exchanger 201. The expansion valve 305 may be an electronic valve. The opening degree of the expansion valve 305 is adjustable, and thus the flow and the pressure of the refrigerant flowing through the expansion valve 305 can be controlled.

The expansion valve 305 may be disposed in the air conditioner indoor unit 20 or the air conditioner outdoor unit 30.

The four-way valve 302 is connected in the refrigerant loop and configured to switch a flow direction of the refrigerant in the refrigerant loop, so as to cause the air conditioner 100 to perform the cooling mode or the heating mode.

The indoor heat exchanger 201 is configured to perform heat-exchange between indoor air and the refrigerant conveyed in the indoor heat exchanger 201. For example, the indoor heat exchanger 201 operates as an evaporator in the cooling mode of the air conditioner 100, so that the refrigerant, which has dissipated heat through the outdoor heat exchanger 303, absorbs heat from the indoor air through the indoor heat exchanger 201 to be evaporated; and the indoor heat exchanger 201 operates as a condenser in the heating mode of the air conditioner 100, so that the refrigerant, which has absorbed heat through the outdoor heat exchanger 303, dissipates heat into the indoor air through the indoor heat exchanger 201 to be condensed.

In some embodiments, the indoor heat exchanger 201 further includes heat-exchange fins, so as to expand a contact area between the indoor air and the refrigerant conveyed in the indoor heat exchanger 201, thereby improving heat-exchange efficiency between the indoor air and the refrigerant.

The indoor fan 207 is configured to suck the indoor air into the air conditioner indoor unit 20 through an indoor air inlet of the air conditioner indoor unit 20 and send the indoor air, after heat-exchange between the indoor air and the indoor heat exchanger 201, out through an indoor air outlet of the air conditioner indoor unit 20. The indoor fan 207 provides power for the flow of the indoor air.

Figure 2:
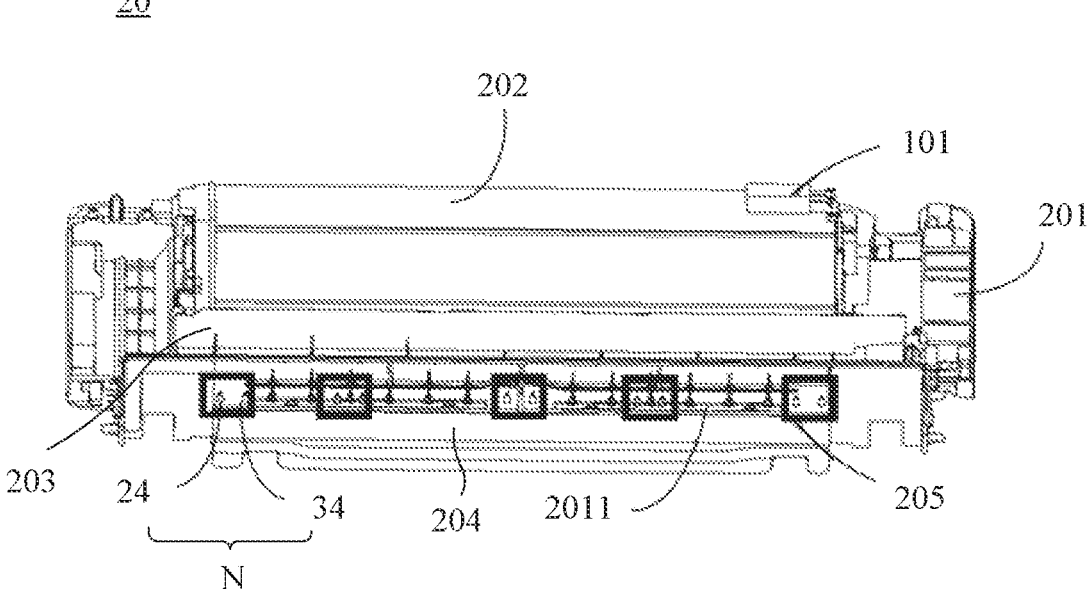
FIG. 2 is a structural diagram of an air conditioner indoor unit, in accordance with some embodiments.

FIG. 2 is a structural diagram of an air conditioner indoor unit, in accordance with some embodiments.

In some embodiments, as shown in FIG. 2, the air conditioner indoor unit 20 further includes a housing 202, an air inlet guide plate 203, and an air outlet guide plate 204. The housing 202 includes an air inlet and an air outlet 2011. The air inlet guide plate 203 is connected with the housing 202, and the air inlet guide plate 203 is disposed at the air inlet, so as to open or close the air inlet. The air outlet guide plate 204 is connected with the housing 202, and the air outlet guide plate 204 is disposed at the air outlet 2011, so as to open or close the air outlet 2011.

The indoor heat exchanger 201 and the indoor fan 207 (referring to FIG. 1) are both disposed in the housing 202. The indoor air may enter the inside of the housing 202 through the air inlet, and flow from the air inlet to the indoor heat exchanger 201 under driving by the indoor fan 207. The air flows through the indoor heat exchanger 201 and exchanges heat with the indoor heat exchanger 201, flows to the air outlet 2011, and finally flows out from the air outlet 2011.

As shown in FIG. 1, the air conditioner 100 further includes a first control device 40. The first control device 40 is configured to control an operating frequency of the compressor 301, the opening degree of the expansion valve 305, a rotation speed of the outdoor fan 304, and a rotation speed of the indoor fan 207. The first control device 40 is connected with the compressor 301, the expansion valve 305, the outdoor fan 304, and the indoor fan 207 by data lines to transmit communication information.

The first control device 40 includes a processor. The processor may include a central processing unit (CPU), a microprocessor, or an application specific integrated circuit (ASIC), and may be configured to perform corresponding operations described with reference to the first control device 40 when the processor executes a program stored on a non-transitory computer readable media coupled to the first control device 40.

Figure 3:
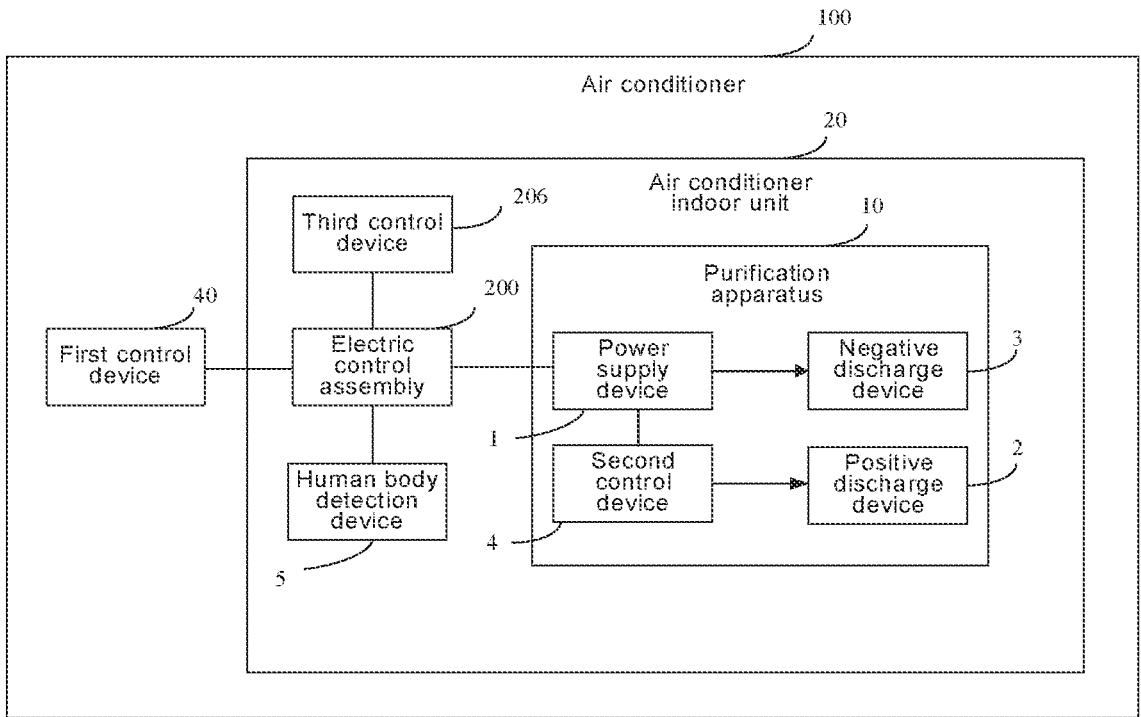
FIG. 3 is a schematic diagram of another air conditioner, in accordance with some embodiments.

FIG. 3 is a schematic diagram of another air conditioner, in accordance with some embodiments.

In some embodiments, as shown in FIG. 3, the air conditioner indoor unit 20 further includes an electric control assembly 200 (e.g., including a CPU or a microprocessor). The air conditioner outdoor unit 30 also includes an electric control assembly (e.g., including a CPU or a microprocessor). The first control device 40 is coupled to the electric control assembly 200 in the air conditioner indoor unit 20 and the electric control assembly in the air conditioner outdoor unit 30. The electric control assembly 200 in the air conditioner indoor unit 20 is configured to control operation of various components (e.g., the indoor fan 207 or the indoor heat exchanger 201) in the air conditioner indoor unit 20 and supply power to the air conditioner outdoor unit 30. The electric control assembly in the air conditioner outdoor unit 30 is configured to control the rotation speed of the outdoor fan 304 (referring to FIG. 1), the opening degree of the expansion valve 305, and the operating frequency of the compressor 301.

The operation modes of the air conditioner indoor unit 20 include a first purification mode and a second purification mode. In a case where the operation mode of the air conditioner indoor unit 20 is the first purification mode, the air conditioner indoor unit 20 makes the surrounding air generate air positive ions and air negative ions. In a case where the operation mode of the air conditioner indoor unit 20 is the second purification mode, the air conditioner indoor unit 20 makes the surrounding air generate air negative ions.

As shown in FIG. 3, the air conditioner indoor unit 20 further includes a purification apparatus 10. The purification apparatus 10 includes a power supply device 1, a positive electrode discharge device 2, a negative electrode discharge device 3, and a second control device 4 (i.e., a control device).

The electric control assembly 200 is coupled to the power supply device 1 and configured to control the power supply device 1 to be turned on or turned off. The power supply device 1 may provide direct current (DC) voltage for the positive electrode discharge device 2 and the negative electrode discharge device 3. The present disclosure does not limit magnitudes of operating voltages of the positive electrode discharge device 2 and the negative electrode discharge device 3. Considering the operating voltages of the positive electrode discharge device 2 and the negative electrode discharge device 3 as 12V as an example, the power supply device 1 may provide a 12V DC voltage for the positive electrode discharge device 2 and the negative electrode discharge device 3. For example, the power supply device 1 is a 12V DC power supply. Alternatively, the power supply device 1 converts a high voltage or an alternating current (AC) voltage into a 12V DC voltage through a voltage conversion circuit.

The negative electrode discharge device 3 is coupled to the power supply device 1 and configured to operate in the first purification mode and the second purification mode.

The positive electrode discharge device 2 is coupled to the power supply device 1 by the second control device 4 and configured to operate in the first purification mode.

Both the positive electrode discharge device 2 and the negative electrode discharge device 3 may be discharged by means of corona discharge or the like. The air positive ions and the air negative ions generated by ionizing air by the positive electrode discharge device 2 and the negative electrode discharge device 3 may effectively kill microorganisms.

In some embodiments, the first purification mode is a sterilization and disinfection mode. In a case where the air conditioner indoor unit 20 starts the first purification mode, the power supply device 1 supplies power to the positive electrode discharge device 2 and the negative electrode discharge device 3. In this case, the positive electrode discharge device 2 discharges to generate a positive high voltage, so that the surrounding air is ionized to generate a large amount of air positive ions; and the negative electrode discharge device 3 discharges to generate a negative high voltage, so that the surrounding air is ionized to generate a large amount of air negative ions.

The air positive ions and the air negative ions are in contact with microorganisms such as bacteria, fungi, viruses, and mites in the air, so as to play a role of killing microorganisms. Alternatively, the air positive ions and the air negative ions neutralize to release energy, so as to play the role of killing microorganisms. After testing, in the first purification mode, an air conditioner 100 equipped with the purification apparatus 10 in the embodiments of the present disclosure has a microorganisms purification rate of over 99% within 1 hour in a space of 30 $m^3$.

In some embodiments, the second purification mode is a refreshing dust reduction mode. In a case where the air conditioner 100 operates in the second purification mode, the positive electrode discharge device 2 does not operate, and the power supply device 1 only supplies power to the negative electrode discharge device 3. In this case, the negative electrode discharge device 3 discharges to generate the negative high voltage, so that the surrounding air is ionized to generate a large amount of air negative ions.

The air negative ions combine with particulate matter in the air such as PM 0.1, PM 0.3, PM 2.5, and PM 10, which may neutralize the positive charges on the surface of most particulate matter and cause the most particulate matter to be settled naturally, thereby reducing a content of particulate matter in the air. In addition, the environment may be filled with a large amount of air negative ions, which may provide users with a high-concentration negative ion environment like a sanatorium. High concentration of air negative ions may promote human metabolism, improve human immunity, and have a refreshing effect, thereby achieving double-effect purification of microorganisms and particulate matter and promoting a transformation of the air conditioner from an air cooling and heating adjustment machine to a comprehensive indoor air steward. In the second purification mode, an air conditioner 100 equipped with the purification apparatus 10 in the embodiments of the present disclosure has a particle purification rate of over 99% within 1 hour in a space of 30 $m^3$, and a clean-air delivery rate (CADR) value exceeds 300 $m^3$/h.

In some embodiments, the second control device 4 is configured to control the power supply device 1 to supply power to the positive electrode discharge device 2 in a case where the operation mode of the air conditioner indoor unit 20 is the first purification mode and control the power supply device 1 to stop supplying power to the positive electrode discharge device 2 in a case where the operation mode of the air conditioner indoor unit 20 is the second purification mode. That is, the second control device 4 in the embodiments of the present disclosure may control whether the power supply device 1 supplies power to the positive electrode discharge device 2 according to the operation mode of the air conditioner indoor unit 20.

The second control device 4 is further configured to determine whether the operation mode of the air conditioner indoor unit 20 is the first purification mode or the second purification mode according to first information. The first information includes at least one of a purification mode trigger instruction, environment information, and operating duration information.

For example, the air conditioner indoor unit 20 further includes a control apparatus, and the control apparatus includes an air conditioner remote controller, a wire controller, an application (APP) in a terminal device, and the like. The user sends an instruction (e.g., the purification mode trigger instruction) to the air conditioner indoor unit 20 through the control apparatus.

The purification mode trigger instruction includes the instruction sent by the user through operating the control apparatus. The environment information may be information of the environment where the air conditioner indoor unit 20 is located (e.g., installation environment information of the air conditioner indoor unit 20). The environment information may include, but is not limited to, at least one of temperature information, wind speed information, light information, and sound information. The operating duration information includes operating duration information of the air conditioner 100 after being turned on, and operating duration information of the purification apparatus 10 in the first purification mode, operating duration information of the purification apparatus 10 in the second purification mode, or the like.

In some embodiments, after the air conditioner 100 is turned on, the indoor fan 207 starts to operate. The user sends the purification mode trigger instruction for operating the first purification mode or the second purification mode by operating the air conditioner remote controller, the wire controller, the APP in the terminal device, or other manners. If the second control device 4 determines that the operation mode of the air conditioner indoor unit 20 is the first purification mode according to the purification mode trigger instruction, the second control device 4 controls the power supply device 1 to supply power to the positive electrode discharge device 2, and the air conditioner indoor unit 20 operates in the first purification mode. If the second control device 4 determines that the operation mode of the air conditioner indoor unit 20 is the second purification mode (e.g., the operation mode of the air conditioner indoor unit 20 is switched from the first purification mode to the second purification mode) according to the purification mode trigger instruction, the second control device 4 controls the power supply device 1 to stop supplying power to the positive electrode discharge device 2, and the air conditioner indoor unit 20 operates the second purification mode.

In some embodiments, in a case where the second control device 4 determines that the operating duration of the air conditioner 100 after being turned on reaches a preset operating duration, and/or the wind speed, the temperature, the light, or the sound reaches a corresponding preset threshold according to the operating duration information of the air conditioner 100 and/or the collected temperature information, wind speed information, light information, and sound information, the second control device 4 determines that the air conditioner indoor unit 20 satisfies a condition of operating the first purification mode and controls the power supply device 1 to supply power to the positive electrode discharge device 2. Alternatively, the second control device 4 determines that the air conditioner indoor unit 20 satisfies a condition of operating the second purification mode and controls the power supply device 1 to stop supplying power to the positive electrode discharge device 2.

In some embodiments, in a case where the purification apparatus 10 is in the operating state, if the second control device 4 determines that the air conditioner indoor unit 20 needs to switch from the first purification mode to the second purification mode according to the purification mode trigger instruction, the environment information, and the operating duration information, the second control device 4 controls the power supply device 1 to stop supplying power to the positive electrode discharge device 2. In this case, the power supply device 1 only supplies power to the negative electrode discharge device 3. Alternatively, if the second control device 4 determines that the air conditioner indoor unit 20 needs to switch from the second purification mode to the first purification mode according to the purification mode trigger instruction, the environment information, and the operating duration information, the second control device 4 controls the power supply device 1 to supply power to the positive electrode discharge device 2. In this case, the power supply device 1 supplies power to the positive electrode discharge device 2 and the negative electrode discharge device 3.

In some embodiments, in a case where the user sends an instruction for exiting the purification function, or the air conditioner 100 is turned off, or the indoor fan 207 stops operating, the power supply device 1 stops supplying power to the positive electrode discharge device 2 and the negative electrode discharge device 3. For example, as shown in FIG. 3, in a case where the user sends the instruction for exiting the purification function, the electric control assembly 200 controls the power supply device 1 to be turned off, so that the power supply device 1 stops supplying power to the positive electrode discharge device 2 and the negative electrode discharge device 3.

The purification apparatus 10 in the embodiments of the present disclosure controls whether the power supply device 1 supplies power to the positive electrode discharge device 2 through the second control device 4, so that the purification mode of the air conditioner indoor unit 20 may be switched between the first purification mode and the second purification mode, thereby implementing two effects of purification and sterilization.

Figure 4:
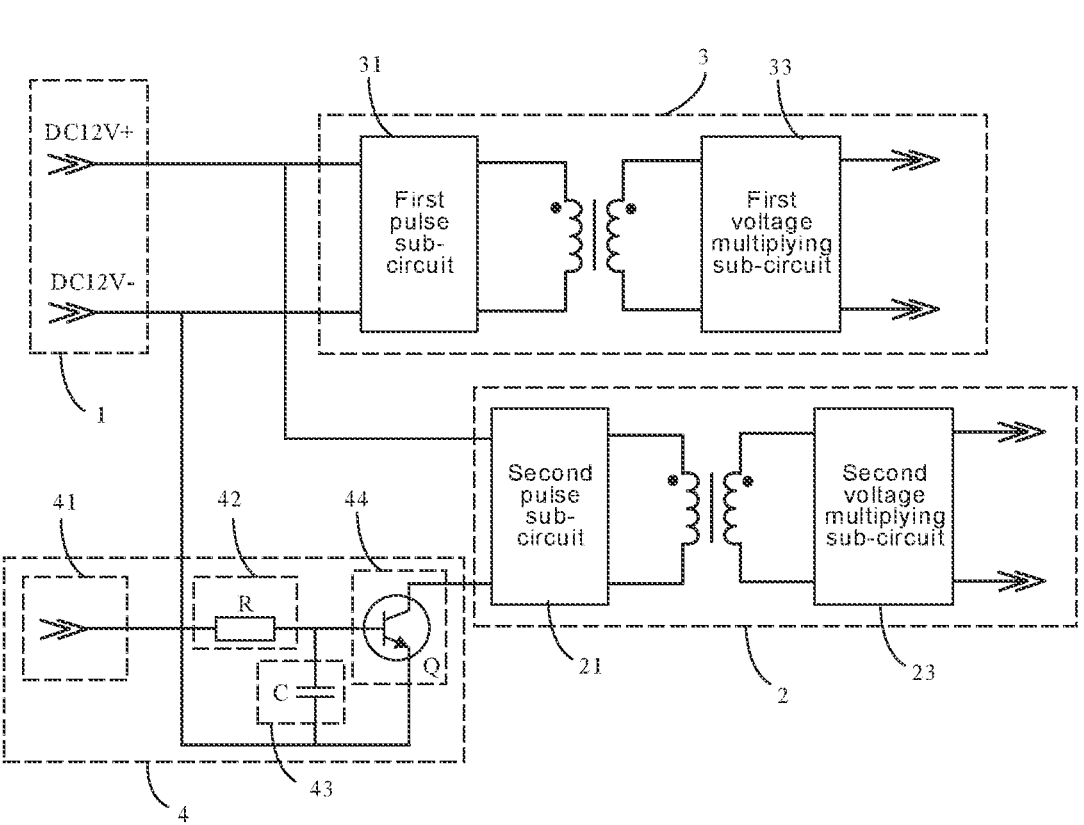
FIG. 4 is a circuit diagram of a purification apparatus, in accordance with some embodiments.

FIG. 4 is a circuit diagram of a purification apparatus, in accordance with some embodiments.

In some embodiments, as shown in FIG. 4, a first input terminal of the negative electrode discharge device 3 is coupled to a positive terminal of the power supply device 1, and a second input terminal of the negative electrode discharge device 3 is coupled to a negative terminal of the power supply device 1. A first input terminal of the positive electrode discharge device 2 is coupled to the positive terminal of the power supply device 1, a second input terminal of the positive electrode discharge device 2 is coupled to a first terminal of the second control device 4, and a second terminal of the second control device 4 is coupled to the negative terminal of the power supply device 1.

The second input terminal of the positive electrode discharge device 2 is set to be coupled to the first terminal of the second control device 4, and the second terminal of the second control device 4 is set to be coupled to the negative terminal of the power supply device 1, so that connection or disconnection between the power supply device 1 and the positive electrode discharge device 2 may be controlled by the second control device 4. Thus, it may be implemented that the positive electrode discharge device 2 to start or stop discharging.

When the operation mode of the air conditioner indoor unit 20 is the second purification mode, the second control device 4 controls the power supply device 1 to stop supplying power to the positive electrode discharge device 2. The positive electrode discharge device 2 stops discharging, and only the negative electrode discharge device 3 discharges and ionizes air to generate a large amount of air negative ions, which play a role of dust reduction and freshness. When the operation mode of the air conditioner indoor unit 20 is the first purification mode, the second control device 4 controls the power supply device 1 to supply power to the positive electrode discharge device 2, and the positive electrode discharge device 2 and the negative electrode discharge device 3 discharge and ionize air to generate a large amount of air positive ions and air negative ions, which play a role of sterilization and disinfection. When the air conditioner indoor unit 20 receives the instruction for exiting the first purification mode from the user, the second control device 4 controls the power supply device 1 to stop supplying power to the positive electrode discharge device 2, and the air conditioner indoor unit 20 exits the first purification mode. When the air conditioner 100 is turned off, the electric control assembly 200 controls the power supply device 1 to be turned off. The power supply device 1 stops supplying power to the positive electrode discharge device 2 and/or the negative electrode discharge device 3, and the air conditioner indoor unit 20 exits the first purification mode or the second purification mode.

In some embodiments, as shown in FIG. 4, the second control device 4 includes a control assembly (e.g., including a first control assembly 41), a resistor assembly 42, a capacitor assembly 43, and a switch assembly 44. The air conditioner indoor unit 20 further includes a control apparatus, and the control apparatus includes an air conditioner remote controller, a wire controller, an APP in a terminal device, and the like. The user sends an instruction (e.g., the purification mode trigger instruction) to the air conditioner indoor unit 20 through the control apparatus.

The first control assembly 41 controls the air conditioner indoor unit 20 to operate the second purification mode or the first purification mode, or exit the second purification mode or the first purification mode, or switch between the second purification mode and the first purification mode according to the instructions sent by the control apparatus, or the operating duration information of the air conditioner 100, and the operating duration information of the air conditioner indoor unit 20 in the first purification mode and the operating duration information of the air conditioner indoor unit 20 the second purification mode.

A first terminal of the resistor assembly 42 is coupled to the first control assembly 41, and the resistor assembly 42 may include a resistor R. A first terminal of the capacitor assembly 43 is coupled to a second terminal of the resistor assembly 42, and the capacitor assembly 43 may include a capacitor C. A second terminal of the capacitor assembly 43 is coupled to the negative terminal of the power supply device 1. A control terminal of the switch assembly 44 is coupled to the second terminal of the resistor assembly 42 and the first terminal of the capacitor assembly 43, a first terminal of the switch assembly 44 is coupled to the second input terminal of the positive electrode discharge device 2, and a second terminal of the switch assembly 44 is coupled to the negative terminal of the power supply device 1. The switch assembly 44 may include a switching transistor Q.

In some embodiments, when the air conditioner 100 is turned on, the air conditioner indoor unit 20 receives the instruction from the air conditioner remote controller, the wire controller, the APP in the terminal device, or by means of other manners to turn on the purification apparatus 10. The first control assembly 41 determines that the operation mode of the air conditioner indoor unit 20 is the first purification mode or the second purification mode according to the instruction, the operating duration information, or the like, and controls the switch assembly 44 to be turned on or turned off. In a case where the switch assembly 44 is turned on, the air conditioner indoor unit 20 operates in the first purification mode, and the power supply device 1 supplies power to the positive electrode discharge device 2 and the negative electrode discharge device 3. The positive electrode discharge device 2 and the negative electrode discharge device 3 discharge simultaneously to ionize air to generate a large amount of air positive ions and air negative ions, so as to achieve sterilization and disinfection. In a case where the switch assembly 44 is turned off, the air conditioner indoor unit 20 operates in the second purification mode, and the power supply device 1 stops supplying power to the positive electrode discharge device 2. The positive electrode discharge device 2 stops discharging, and only the negative electrode discharge device 3 discharges to ionize air to generate a large amount of air negative ions, so as to achieve dust reduction and freshness.

Figure 5:
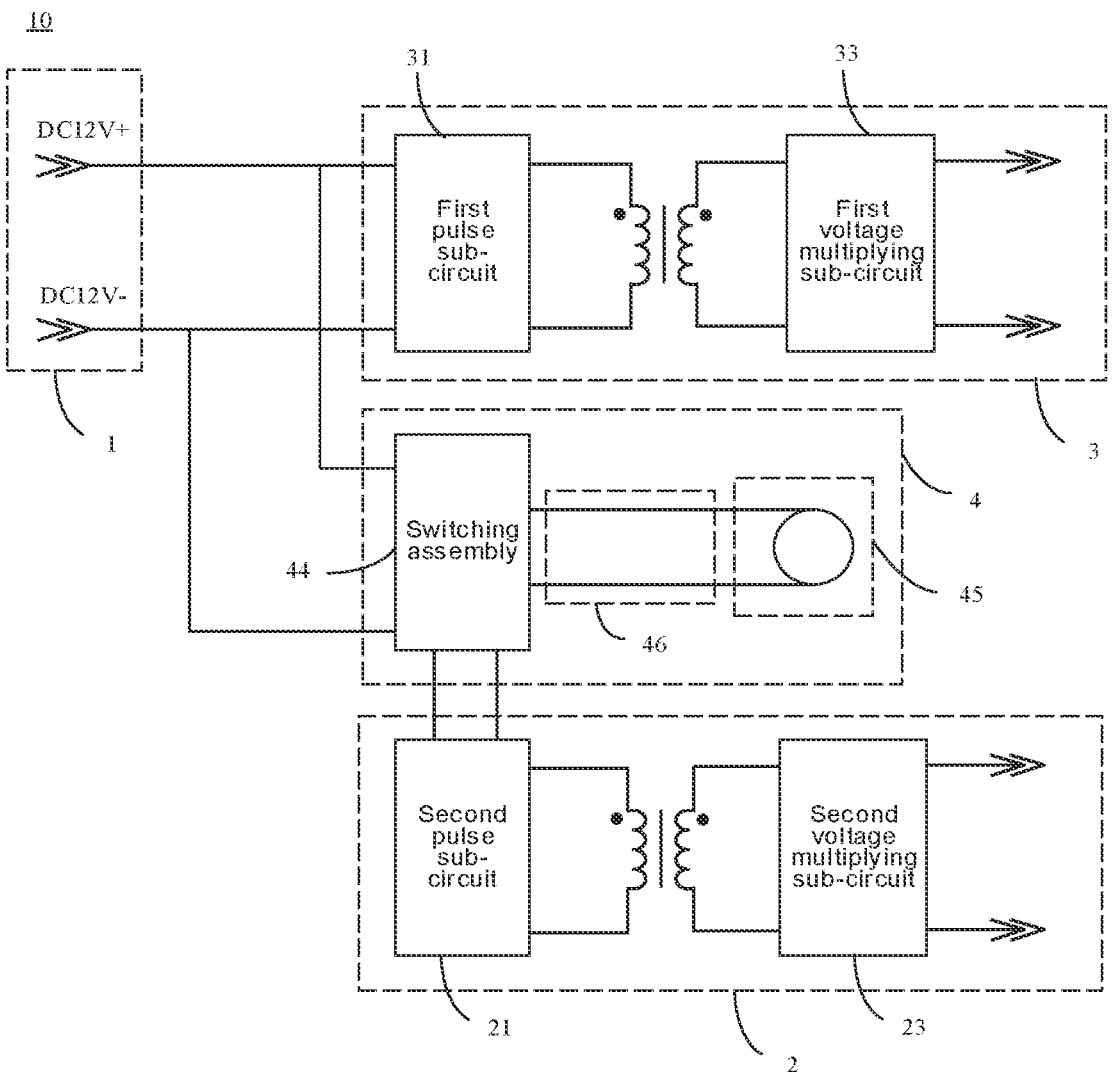
FIG. 5 is a circuit diagram of another purification apparatus, in accordance with some embodiments.

FIG. 5 is a circuit diagram of another purification apparatus, in accordance with some embodiments.

In some embodiments, as shown in FIG. 5, a first input terminal of the negative electrode discharge device 3 is coupled to a positive terminal of the power supply device 1, and a second input terminal of the negative electrode discharge device 3 is coupled to a negative terminal of the power supply device 1. Input terminals of the positive electrode discharge device 2 are coupled to first terminals of the second control device 4, and second terminals of the second control device 4 are coupled to the power supply device 1.

In some embodiments, as shown in FIG. 5, the second control device 4 further includes a switch assembly 44, a sensing assembly 45, and the control assembly (e.g., including a second control assembly 46). The sensing assembly 45 is coupled to the second control assembly 46 and configured to collect the environment information. The sensing assembly 45 includes at least one of a temperature sensor, a wind speed sensor, a photosensitive sensor, and an acoustic sensor. For example, the sensing assembly 45 includes the wind speed sensor, the temperature sensor, the photosensitive sensor, the sound sensor, or the like, and the sensing assembly 45 is configured to collect wind speed information, temperature information, light information, sound information, or the like. The photosensitive sensor may include a photosensitive element, and the photosensitive element is configured to collect a light signal such as a specific infrared signal.

The second control assembly 46 is coupled to the sensing assembly 45 and configured to control the switch assembly 44 to be turned on or turned off according to the environment information or a mode switching instruction. For example, in a case where the sensing assembly 45 collects the temperature information, the wind speed information, the light information, the sound information, and the like, and the second control assembly 46 determines that at least one of the temperature information, the wind speed information, the light information, and the sound information reaches the corresponding preset threshold according to the environment information collected by the sensing assembly 45, the second control assembly 46 controls the switch assembly 44 to be turned on or turned off, so that the air conditioner indoor unit 20 operates in the first purification mode or the second purification mode. Alternatively, in a case where the second control assembly 46 receives the mode switching instruction (e.g., an infrared signal, or a voice control instruction of the user) sent by the user through the air conditioner remote controller, the wire controller, and the like, the second control assembly 46 controls the switch assembly 44 to be turned on or turned off, so that the air conditioner indoor unit 20 operates in the first purification mode or the second purification mode.

A control terminal of the switch assembly 44 is coupled to the second control assembly 46, a third terminal and a fourth terminal of the switch assembly 44 are coupled to the power supply device 1, and a first terminal and a second terminal of the switch assembly 44 are coupled to the input terminals of the positive electrode discharge device 2. The switch assembly 44 is configured to be turned on or turned off in response to a control signal of the second control assembly 46.

When the second control assembly 46 controls the switch assembly 44 to be turned off, the air conditioner indoor unit 20 operates in the second purification mode. The power supply device 1 stops supplying power to the positive electrode discharge device 2, and the positive electrode discharge device 2 stops discharging. The negative electrode discharge device 3 continues to discharge to ionize air to generate a large amount of air negative ions, so as to play the role of dust reduction and freshness. When the second control assembly 46 controls the switch assembly 44 to be turned on, the air conditioner indoor unit 20 operates in the first purification mode. The power supply device 1 supplies power to the positive electrode discharge device 2 and the negative electrode discharge device 3, and the positive electrode discharge device 2 and the negative electrode discharge device 3 discharge to ionize air to generate a large amount of air positive ions and air negative ions, so as to play the role of sterilization and disinfection.

For example, the second control device 4 includes at least two processors, and any two of the at least two processors are the first control assembly 41 and the second control assembly 46. The processor may include a central processing unit (CPU), a microprocessor, or an application specific integrated circuit (ASIC), and may be configured to perform corresponding operations described with reference to the second control device 4 when the processor executes a program stored on a non-transitory computer readable media coupled to the second control device 4.

In some embodiments, as shown in FIG. 5, the first input terminal of the negative electrode discharge device 3 is coupled to the positive terminal of the power supply device 1, and the second input terminal of the negative electrode discharge device 3 is coupled to the negative terminal of the power supply device 1. A first input terminal of the positive electrode discharge device 2 is coupled to the first terminal of the switch assembly 44, and a second input terminal of the positive electrode discharge device 2 is coupled to the second terminal of the switch assembly 44. A third terminal of the switch assembly 44 is coupled to the positive terminal of the power supply device 1, and a fourth terminal of the switch assembly 44 is coupled to the negative terminal of the power supply device 1.

Figure 6:
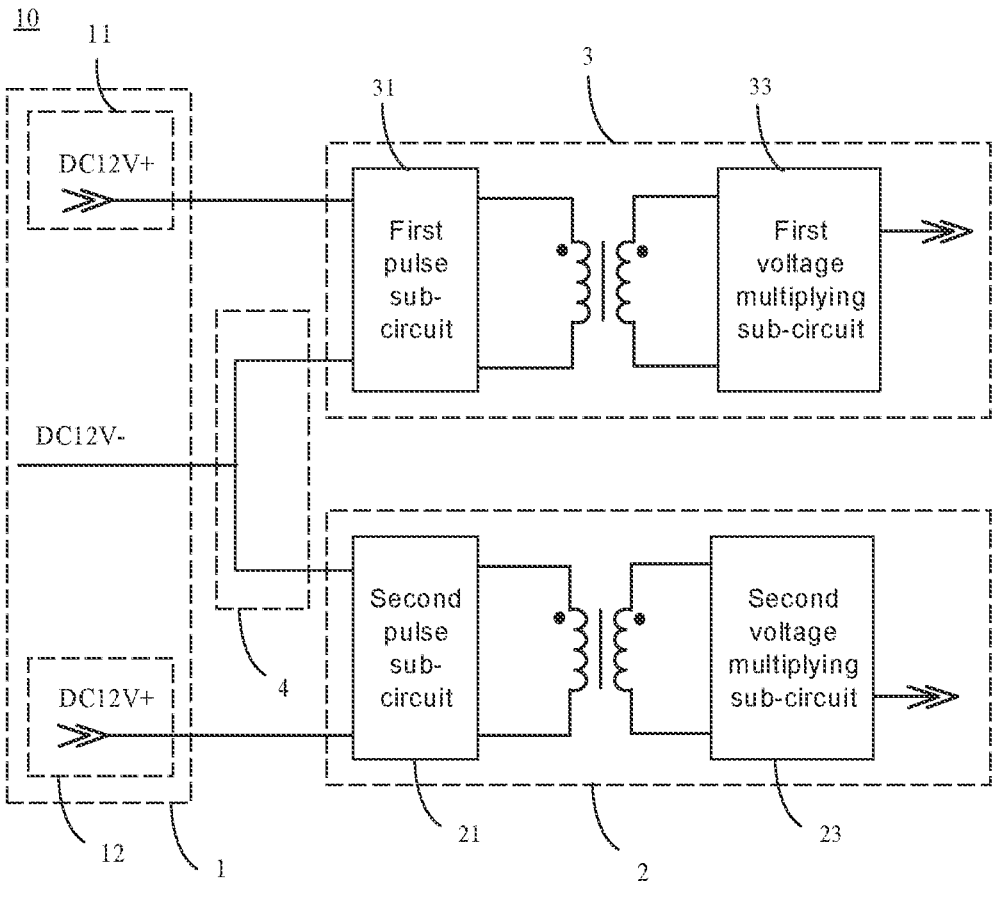
FIG. 6 is a circuit diagram of yet another purification apparatus, in accordance with some embodiments.

FIG. 6 is a circuit diagram of yet another purification apparatus, in accordance with some embodiments.

In some embodiments, as shown in FIG. 6, the power supply device 1 includes a first power supply 11 and a second power supply 12, both the first power supply 11 and the second power supply 12 are coupled to the second control device 4, and both the positive electrode discharge device 2 and the negative electrode discharge devices 3 are coupled to the second control device 4. The first power supply 11 and the second power supply 12 supply power to the negative electrode discharge device 3 and the positive electrode discharge device 2, respectively.

As shown in FIG. 6, a first input terminal of the negative electrode discharge device 3 is coupled to a positive terminal of the first power supply 11, and a second input terminal of the negative electrode discharge device 3 is coupled to a first terminal of the second control device 4. A first input terminal of the positive electrode discharge device 2 is coupled to a positive terminal of the second power supply 12, and a second input terminal of the positive electrode discharge device 2 is coupled to a second terminal of the second control device 4. A third terminal of the second control device 4 is coupled to negative terminals of the first power supply 11 and the second power supply 12.

In some embodiments, the second control device 4 controls the first power supply 11 to supply power or stop supplying power to the negative electrode discharge device 3 and controls the second power supply 12 to supply power or stop supplying power to the positive electrode discharge device 2. That is, the negative electrode discharge device 3 and the positive electrode discharge device 2 may be separately controlled by the second control device 4, so as to control the generation of air positive ions and air negative ions.

In a case where the operation mode of the air conditioner indoor unit 20 is the first purification mode, the second control device 4 controls the first power supply 11 to supply power to the negative electrode discharge device 3 and controls the second power supply 12 to supply power to the positive electrode discharge device 2. In a case where the operation mode of the air conditioner indoor unit 20 is the second purification mode, the second control device 4 controls the first power supply 11 to supply power to the negative electrode discharge device 3 and controls the second power supply 12 to stop supplying power to the positive electrode discharge device 2. That is, the air conditioner indoor unit 20 in the embodiments of the present disclosure controls whether the first power supply 11 supplies power to the negative electrode discharge device 3 and whether the second power supply 12 supplies power to the positive electrode discharge device 2 through the second control device 4, so as to separately control the power supplying of the positive electrode discharge device 2 and the negative electrode discharge device 3.

Figure 7:
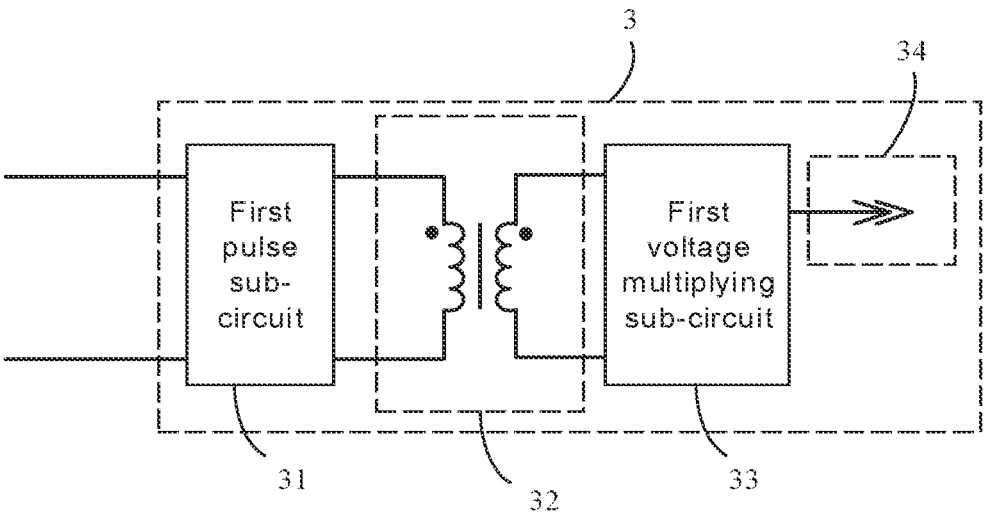
FIG. 7 is a circuit diagram of a negative electrode discharge device, in accordance with some embodiments.

FIG. 7 is a circuit diagram of a negative electrode discharge device, in accordance with some embodiments.

In some embodiments, as shown in FIG. 7, the negative electrode discharge device 3 includes a first pulse sub-circuit 31, a first voltage transformation sub-circuit 32, a first voltage multiplying sub-circuit 33, and a negative discharge electrode 34.

The first pulse sub-circuit 31 is coupled to the power supply device 1. In a case where the power supply device 1 supplies power to the negative electrode discharge device 3, the first pulse sub-circuit 31 is configured to convert a power signal output by the power supply device 1 to a first AC signal. Input terminals of the first voltage transformation sub-circuit 32 are coupled to output terminals of the first pulse sub-circuit 31. The first voltage transformation sub-circuit 32 is configured to transform a voltage of the first AC signal output by the first pulse sub-circuit 31 and output a first voltage-transformed signal. Input terminals of the first voltage multiplying sub-circuit 33 are coupled to output terminals of the first voltage transformation sub-circuit 32. The first voltage multiplying sub-circuit 33 is configured to multiply a voltage of the first voltage-transformed signal output by the first voltage transformation sub-circuit 32 and output a first voltage-multiplied signal. The negative discharge electrode 34 is coupled to an output terminal of the first voltage multiplying sub-circuit 33 and configured to discharge due to the excitation of the first voltage-multiplied signal output by the first voltage multiplying sub-circuit 33, so as to make the surrounding air generate air negative ions.

It can be understood that the voltage multiplying (i.e., the voltage multiplying rectification) involved in the embodiments of the present disclosure refers to rectifying an AC voltage with a low voltage value into a DC voltage with a high voltage value by using a rectifier diode with a high withstand voltage performance and a capacitor. Usually, the DC voltage with a high voltage value is an integer multiple (e.g., double, triple) of the AC voltage with a low voltage value.

Figures 8, 9:
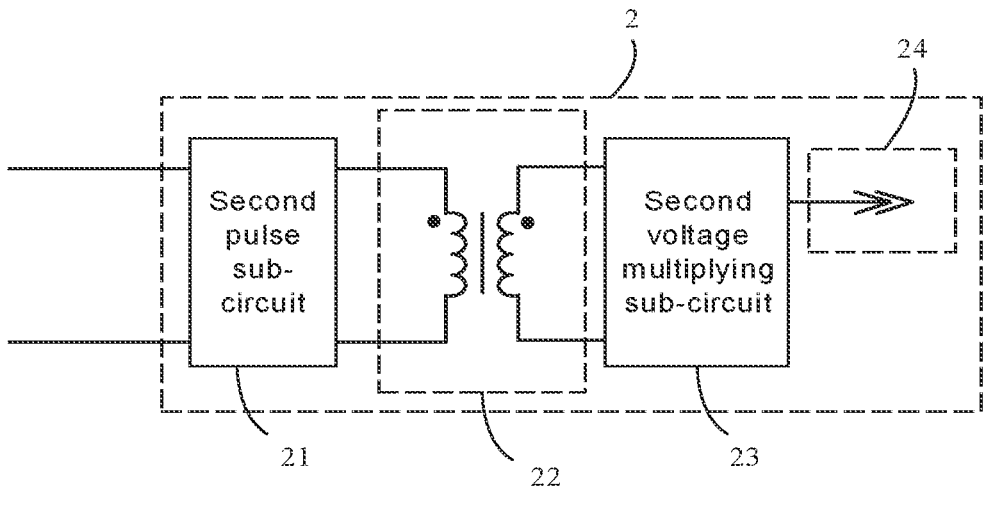
FIG. 8 is a circuit diagram of a positive electrode discharge device, in accordance with some embodiments.
FIG. 9 is a flow diagram of a purification control method of an air conditioner indoor unit, in accordance with some embodiments.

FIG. 8 is a circuit diagram of a positive electrode discharge device, in accordance with some embodiments.

In some embodiments, as shown in FIG. 8, the positive electrode discharge device 2 includes a second pulse sub-circuit 21, a second voltage transformation sub-circuit 22, a second voltage multiplying sub-circuit 23, and a positive discharge electrode 24.

The second pulse sub-circuit 21 is coupled to the power supply device 1. In a case where the power supply device 1 supplies power to the positive electrode discharge device 2, the second pulse sub-circuit 21 is configured to convert a power signal output by the power supply device 1 into a second AC signal. Input terminals of the second voltage transformation sub-circuit 22 are coupled to output terminals of the second pulse sub-circuit 21, and the second voltage transformation sub-circuit 22 is configured to transform a voltage of the second AC signal output by the second pulse sub-circuit 21 and output a second voltage-transformed signal. Input terminals of the second voltage multiplying sub-circuit 23 are coupled to output terminals of the second voltage transformation sub-circuit 22, and the second voltage multiplying sub-circuit 23 is configured to multiply a voltage of the second voltage-transformed signal output by the second voltage transformation sub-circuit 22 and output a second voltage-multiplied signal. The positive discharge electrode 24 is coupled to an output terminal of the second voltage multiplying sub-circuit 23 and configured to discharge due to the excitation of the second voltage-multiplied signal output by the second voltage multiplying sub-circuit 23, so as to make the surrounding air generate air positive ions.

In some embodiments, the air outlet guide plate 204, the indoor heat exchanger 201, and the indoor fan 207 are coupled to the electric control assembly 200. In a case where the air conditioner indoor unit 20 operates in the first purification mode or the second purification mode, the air outlet guide plate 204 is in a fully open state, and a temperature of the indoor heat exchanger 201 is less than or equal to a predetermined temperature, and the electric control assembly 200 is further configured to control the indoor fan 207 to operate at a first wind speed for a first predetermined time.

It will be noted that the above fully open state refers to that an air outlet angle of the air outlet guide plate 204 is an angle at which an air outlet distance is the largest.

The predetermined temperature may be 35° C., and the first predetermined time is in a range from 1 min to 5 min, inclusive. For example, the first predetermined time is 1 min, 2 min, 3 min, 4 min or 5 min. The present disclosure does not limit specific numerical values of the predetermined temperature and the first predetermined time.

After the indoor fan 207 operates at the first wind speed for the first predetermined time, the electric control assembly 200 is further configured to control the indoor fan 207 to operate at the second wind speed, and the second wind speed is greater than the first wind speed. Alternatively, in a case where the air conditioner indoor unit 20 operates in the first purification mode or the second purification mode, the air outlet guide plate 204 is in the fully open state, and the temperature of the indoor heat exchanger 201 is greater than the predetermined temperature, and the electric control assembly 200 is further configured to control the indoor fan 207 to operate at the second wind speed, and the second wind speed is greater than the first wind speed.

Here, the first wind speed may refer to the indoor fan 207 operating at a low speed, and the second wind speed may refer to the indoor fan 207 operating at a high speed. In this way, it is convenient to an increase in temperature of a discharge terminal of a discharge device, and it may prevent cold air from lowering the temperature of the discharge terminal.

In some embodiments, as shown in FIG. 3, the air conditioner indoor unit 20 further includes a human body detection device 5. The human body detection device 5 is coupled to the electric control assembly 200, and the electric control assembly 200 is coupled to the power supply device 1. The human body detection device 5 is configured to detect whether there are people in the environment space. The electric control assembly 200 is configured to cause the power supply device 1 to be turned on in response to the human body detection device 5 detecting that there are no people in the environment space, so that the air conditioner indoor unit 20 operates in the first purification mode or the second purification mode. The electric control assembly 200 is further configured to cause the power supply device 1 to be turned off in response to the human body detection device 5 detecting that there are people in the environment space, so that the air conditioner indoor unit 20 pauses or stops operating in the first purification mode or the second purification mode. When the air conditioner indoor unit 20 operates in the first purification mode or the second purification mode, air positive ions and/or air negative ions will be generated. In order to avoid the adverse effects of air positive ions and/or air negative ions on the human body, the air conditioner indoor unit 20 may operate in the first purification mode or the second purification mode in a case where there are no people.

For example, the human detection device 5 may include at least one of an infrared sensor, an ultrasonic sensor, or an image sensor.

In some embodiments, as shown in FIG. 2, the air conditioner 100 includes the above air conditioner indoor unit 20, and the above air conditioner indoor unit 20 includes the above purification apparatus 10.

The purification apparatus 10 includes a boost circuit 101, at least one positive discharge electrode 24, and at least one negative discharge electrode 34. The boost circuit 101 may be composed of a pulse sub-circuit, a voltage transformation sub-circuit, a voltage multiplying sub-circuit, and the like. For example, the boost circuit 101 includes the first pulse sub-circuit 31, the first voltage transformation sub-circuit 32, the first voltage multiplying sub-circuit 33, the second pulse sub-circuit 21, the second voltage transformation sub-circuit 22, the second voltage multiplying sub-circuit 23, and the like. The boost circuit 101 is configured to increase the voltage and convert an input power signal to a voltage-multiplied signal, so as to excite the discharge electrodes to discharge. The boost circuit 101 is disposed on an end plate of the indoor heat exchanger 201 for easy installation.

The at least one positive discharge electrode 24 and the at least one negative discharge electrode 34 constitute a discharge terminal N of a discharge device, and the discharge terminal N of the discharge device is disposed at the air outlet 2011 of the air conditioner indoor unit 20. In this way, when the air conditioner 100 blows out air, it is convenient to quickly deliver air positive ions and/or air negative ions generated by the positive discharge electrode 24 and/or the negative discharge electrode 34 to the entire room and continuously deliver new air to be treated to the discharge electrodes, so as to accelerate the circulation of air positive ions and/or air negative ions indoors and improve air treatment efficiency. For example, when the operation mode of the air conditioner indoor unit 20 is the first purification mode, it may have an efficient purification effect on pollutants such as microorganisms and particulate matter. When the operation mode of the air conditioner indoor unit 20 is the second purification mode, it may quickly fill the room with a large amount of air negative ions, so as to provide users with the high-concentration negative ion environment.

When the air conditioner indoor unit 20 operates in the first purification mode or the second purification mode, the temperature of the discharge terminal N of the discharge device is in a range from 30° C. to 60° C., inclusive. Setting the temperature of the discharge terminal N within the above temperature range may promote the generation of air positive ions and air negative ions.

In some embodiments, as shown in FIG. 2, the air conditioner indoor unit 20 further includes a base 205. The at least one positive discharge electrode 24 includes a plurality of positive discharge electrodes 24, and the at least one negative discharge electrode 34 includes a plurality of negative discharge electrodes 34. The plurality of positive discharge electrodes 24 and the plurality of negative discharge electrodes 34 are all disposed on the base 205, and the base 205 is disposed at the air outlet 2011.

A positive discharge electrode 24 and a negative discharge electrode 34 are a set of discharge electrodes, and a plurality of sets of discharge electrodes constitute discharge terminals N of a plurality of discharge devices. The discharge terminals N of the plurality of discharge devices are installed in a form of an integral structure. For example, the discharge terminals N of the plurality of discharge devices may be inserted in the base 205 and fixed at the air outlet 2011 by buckles, so as to ensure that the discharge terminals N of the plurality of discharge devices are in full contact with the air. In this way, a large amount of air positive ions and/or air negative ions may be generated during the discharge of the discharge electrodes, and the circulation of air positive ions and/or air negative ions may be accelerated, thereby improving air treatment efficiency.

The embodiments of the present disclosure further provide a purification control method of an air conditioner indoor unit. The air conditioner indoor unit may be the above air conditioner indoor unit 20.

FIG. 9 is a flow diagram of a purification control method of an air conditioner indoor unit, in accordance with some embodiments.

As shown in FIG. 9, the purification control method includes steps 1 to 3.

In step 1, the air conditioner indoor unit 20 detects whether there are people in the environment space. If not, step 2 is performed. If so, step 3 is performed.

In step 2, the air conditioner indoor unit 20 operates in a first purification mode or a second purification mode.

In step 3, the air conditioner indoor unit 20 pauses or stops operating in the first purification mode or the second purification mode.

For example, when a human body detection device 5 detects that there are no people in the environment space, an electric control assembly 200 receives a signal from the human body detection device 5 and makes the power supply device 1 turn on. When the human body detection device 5 detects that there are people in the environment space, the electric control assembly 200 receives another signal from the human body detection device 5 and makes the power supply device 1 turn off.

The air conditioner indoor unit 20 will generate air positive ions and/or air negative ions when operating in the first purification mode or the second purification mode. In order to avoid the adverse effects of air positive ions and/or air negative ions on the human body, the air conditioner indoor unit 20 may operate in the first purification mode or the second purification mode in a case where there are no people. It can be understood that, when the user is in the room and the air conditioner indoor unit 20 operates in the first purification mode or the second purification mode, existence of the human body will adversely affect uniform distribution of air positive ions and/or air negative ions, thereby resulting in incomplete purification. Therefore, in a case where the human body detection device 5 detects that there are people in the environment space, the air conditioner indoor unit 20 pauses or stops operating in the purification mode. The air conditioner indoor unit 20 operates in the first purification mode or the second purification mode after determining that there are no people in the room, so that active substances such as air positive ions, air negative ions, and free radicals may survive long and are evenly distributed in space. Moreover, a whole-room microorganism purification effect of the air conditioner indoor unit 20 may be improved without affecting daily life of people, and the purification time may be shortened, thereby implementing efficient and rapid air purification of the room.

Figure 10:
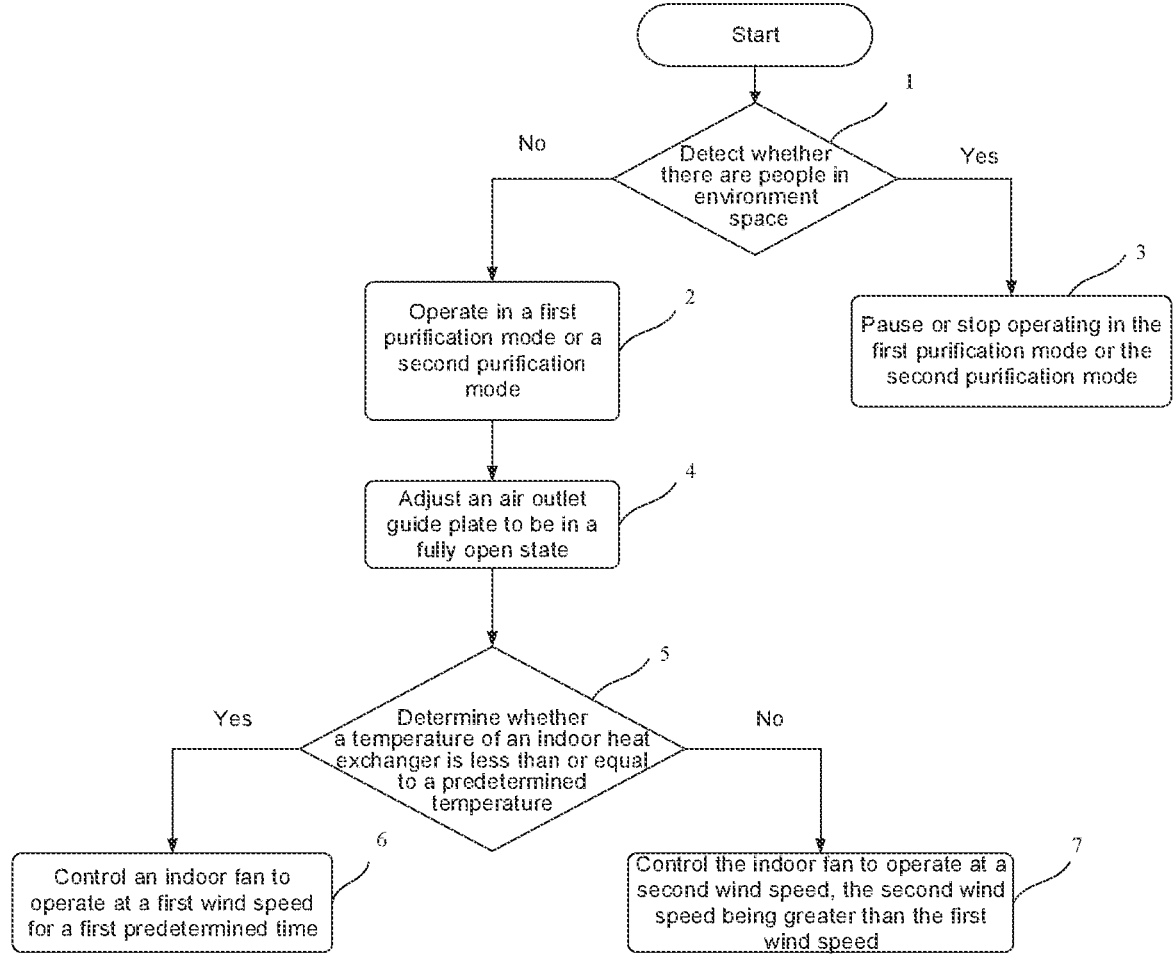
FIG. 10 is a flow diagram of another purification control method of an air conditioner indoor unit, in accordance with some embodiments.

FIG. 10 is a flow diagram of another purification control method of an air conditioner indoor unit, in accordance with some embodiments.

In some embodiments, as shown in FIG. 10, after step 2, the purification control method further includes steps 4 to 7.

In step 4, when the air conditioner indoor unit 20 operates in the first purification mode or the second purification mode, the air conditioner indoor unit 20 adjusts an air outlet guide plate 204 to be in a fully open state.

In step 5, it is determined whether a temperature of the indoor heat exchanger 201 is less than or equal to a predetermined temperature. If so, step 6 is performed. If not, step 7 is performed.

For example, the predetermined temperature is 35° C. The present disclosure does not limit a specific numerical value of the predetermined temperature.

In step 6, the air conditioner indoor unit 20 controls the indoor fan 207 to operate at a first wind speed for a first predetermined time.

The first predetermined time may be in a range from 1 min to 5 min, inclusive. For example, the first predetermined time is 1 min, 2 min, 3 min, 4 min or 5 min. The present disclosure does not limit a specific numerical value of the first predetermined time.

In step 7, the air conditioner indoor unit 20 controls the indoor fan 207 to operate at a second wind speed, and the second wind speed is greater than the first wind speed.

Here, the first wind speed may refer to that the indoor fan 207 operates at a low speed, and the second wind speed may refer to that the indoor fan 207 operates at a high speed. In this way, it is convenient to an increase in temperature of a discharge terminal of a discharge device, and it may prevent cold air from lowering the temperature of the discharge terminal.

When the temperature of the heat exchanger reaches the predetermined temperature, the fan operates at maximum power and drives the indoor fan 207 to rotate. In this way, the transportation process of active groups may be prevented from being hindered, and the active groups such as air positive ions, air negative ions, and hydroxyl radicals may be promoted to quickly distribute in the indoor space. In addition, the air to be treated may be quickly guided to the discharge terminal of the discharge device, thereby improving the efficiency of ion generation and increasing the amount of air positive ions and air negative ions.

Figure 11:
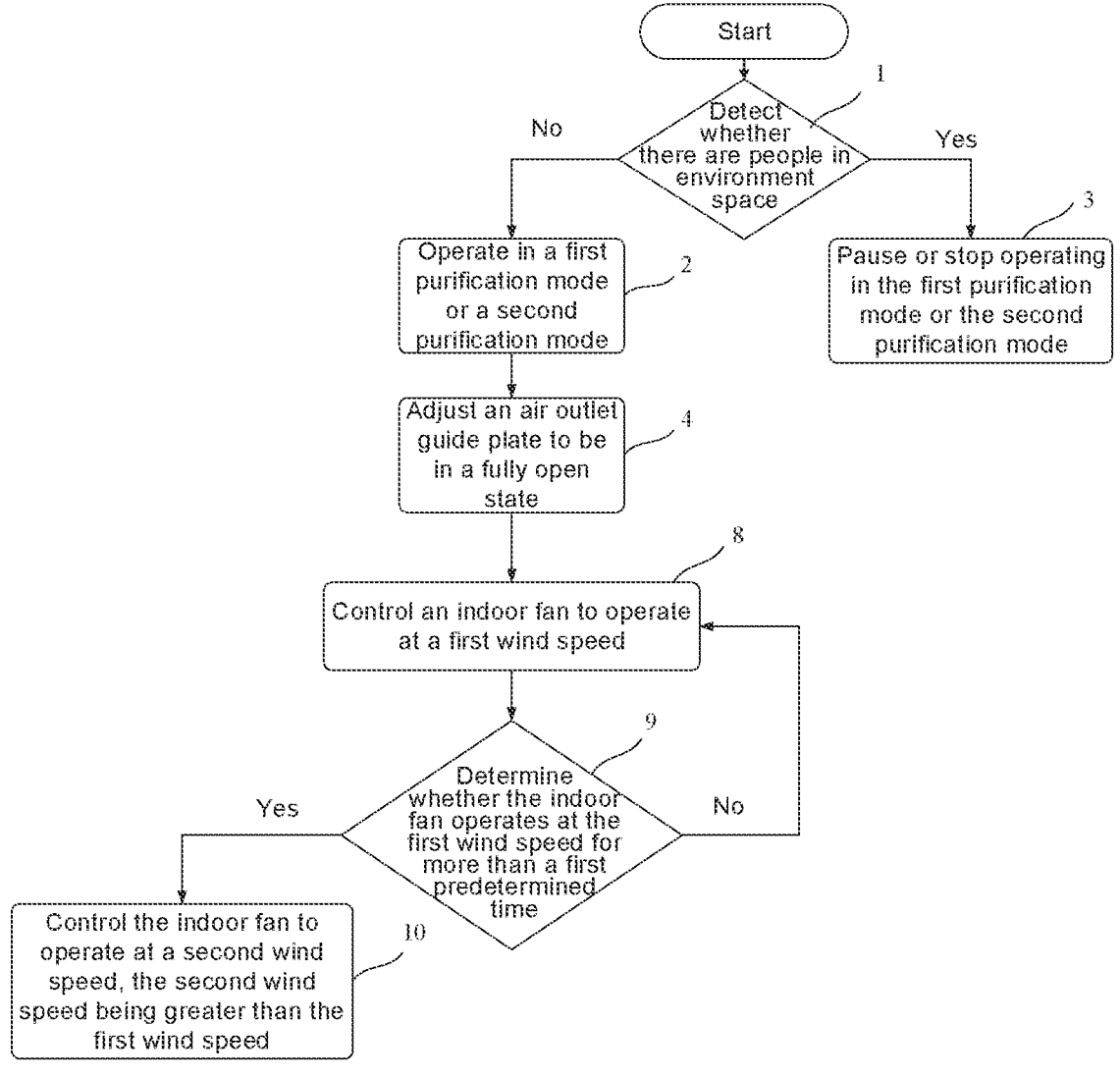
FIG. 11 is a flow diagram of yet another purification control method of an air conditioner indoor unit, in accordance with some embodiments.

FIG. 11 is a flow diagram of yet another purification control method of an air conditioner indoor unit, in accordance with some embodiments.

In some embodiments, as shown in FIG. 11, after step 4, the purification control method further includes steps 8 to 10.

In step 8, the air conditioner indoor unit 20 controls the indoor fan 207 to operate at a first wind speed.

In step 9, it is determined whether the indoor fan 207 operates at the first wind speed for more than a first predetermined time. If so, step 10 is performed. If not, step 8 is re-performed.

In step 10, the air conditioner indoor unit 20 controls the indoor fan 207 to operate at a second wind speed, and the second wind speed is greater than the first wind speed.

The indoor fan 207 operates at the first wind speed for the first predetermined time and then operates at the second wind speed, which is convenient to an increase in temperature of the discharge terminal of the discharge device, and it may prevent cold air from lowering the temperature of the discharge terminal.

When the indoor fan 207 operates at the first wind speed for more than the first predetermined time, the indoor fan 207 operates at the second wind speed. In this way, active groups such as air positive ions, air negative ions, and hydroxyl radicals may be promoted to quickly distribute in the indoor space. In addition, the air to be treated may be quickly guided to the discharge terminal of the discharge device, thereby improving the efficiency of ion generation.

Figure 12:
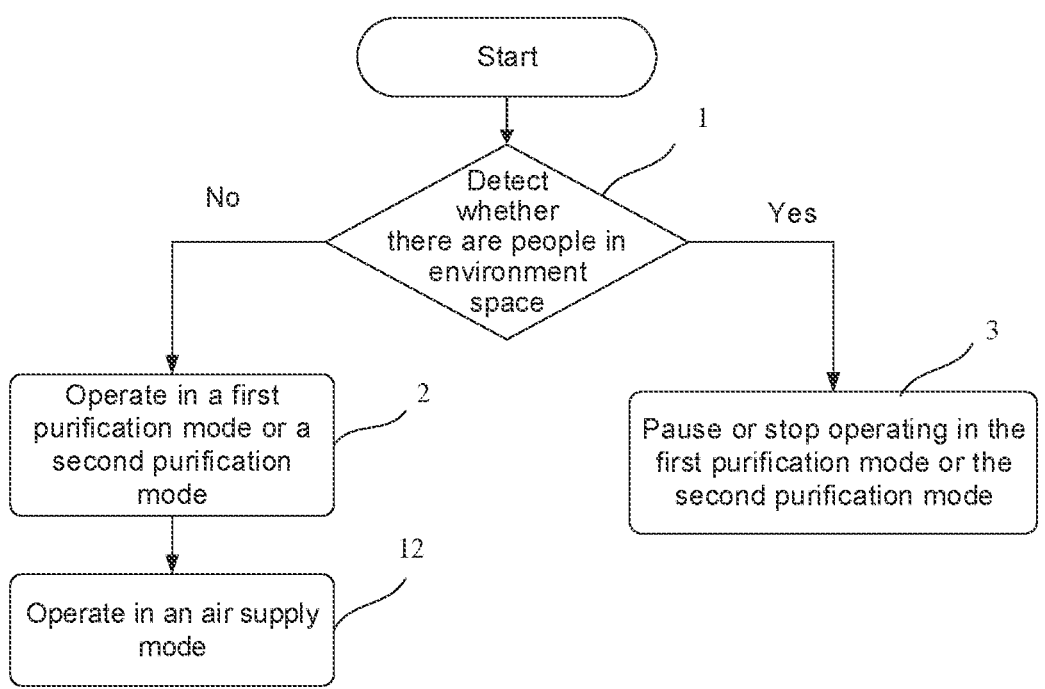
FIG. 12 is a flow diagram of yet another purification control method of an air conditioner indoor unit, in accordance with some embodiments.

FIG. 12 is a flow diagram of yet another purification control method of an air conditioner indoor unit, in accordance with some embodiments.

In some embodiments, the operation mode of the air conditioner indoor unit 20 further includes an air supply mode. As shown in FIG. 12, after step 2, the purification control method further includes a step 12.

In step 12, when the operation mode of the air conditioner indoor unit 20 is the first purification mode or the second purification mode, the air conditioner indoor unit 20 further operates in the air supply mode.

For example, the air outlet of the air conditioner indoor unit 20 is provided with a swing blade. When the air conditioner indoor unit 20 operates in the first purification mode or the second purification mode and operates in the air supply mode simultaneously, the air conditioner indoor unit 20 controls all of the air inlet guide plate 203, the air outlet guide plate 204, and the swing blade at the air outlet to be in the fully open states. In this way, the airflow may flow out quickly, the diffusion speed of negative ions may be accelerated, and the purification efficiency of the air conditioner indoor unit 20 may be improved.

Figure 13:
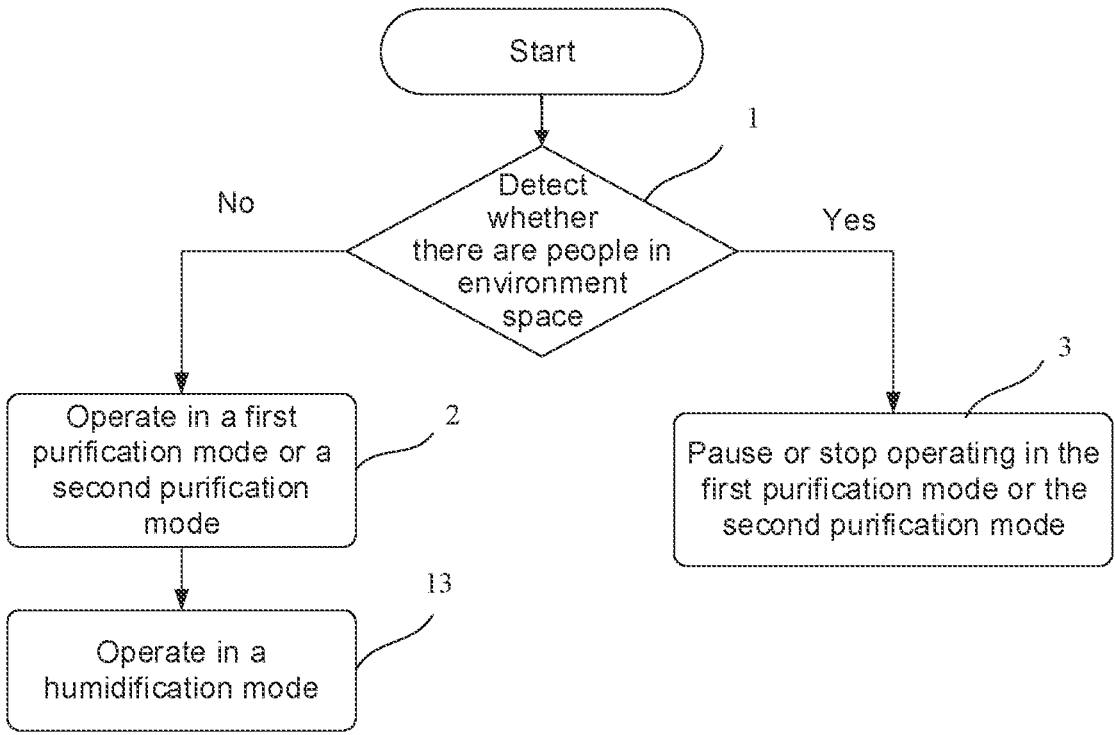
FIG. 13 is a flow diagram of yet another purification control method of an air conditioner indoor unit, in accordance with some embodiments.

FIG. 13 is a flow diagram of yet another purification control method of an air conditioner indoor unit, in accordance with some embodiments.

In some embodiments, the operation mode of the air conditioner indoor unit 20 further includes a humidification mode. As shown in FIG. 13, after step 2, the purification control method further includes a step 13.

In step 13, when the operation mode of the air conditioner indoor unit 20 is the first purification mode or the second purification mode, the air conditioner indoor unit 20 further operates in the humidification mode.

For example, the air conditioner indoor unit 20 includes a humidifying device. When the operation mode of the air conditioner indoor unit 20 is the first purification mode or the second purification mode, the humidifying device is turned on to perform humidification. Alternatively, the air conditioner indoor unit 20 is linked with a bound humidifier to humidify the indoor environment.

Figure 14:
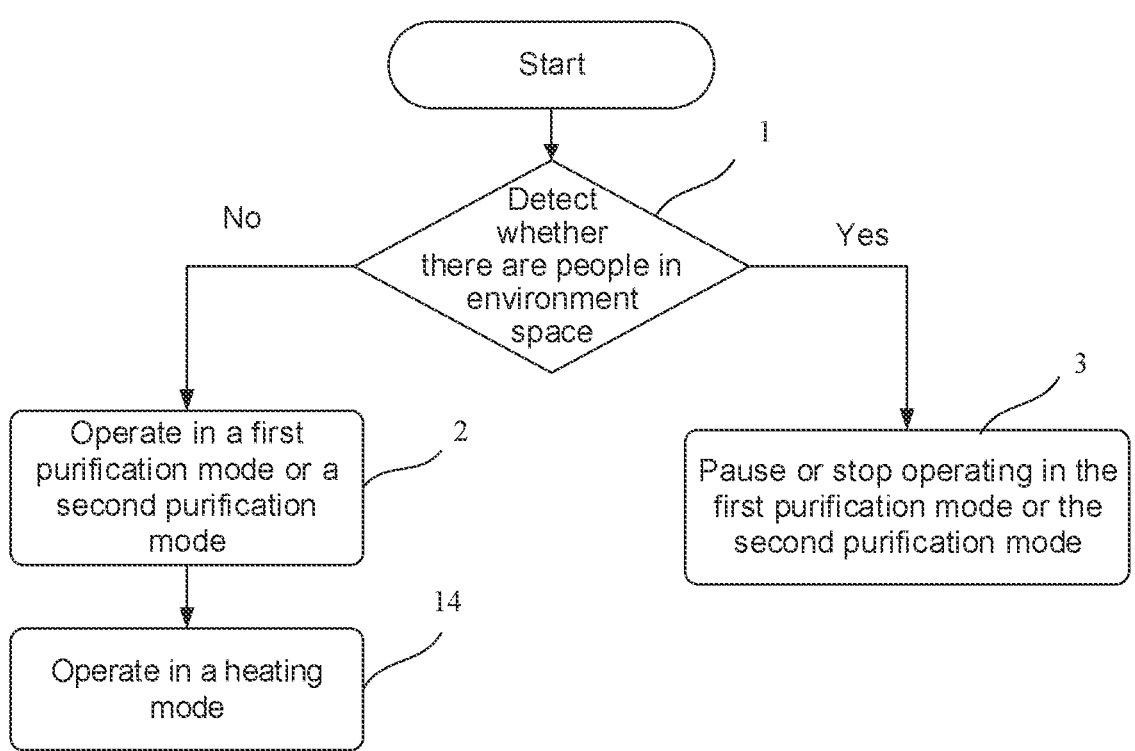
FIG. 14 is a flow diagram of yet another purification control method of an air conditioner indoor unit, in accordance with some embodiments.

FIG. 14 is a flow diagram of yet another purification control method of an air conditioner indoor unit, in accordance with some embodiments.

In some embodiments, the operation mode of the air conditioner indoor unit 20 further includes a heating mode. In this case, as shown in FIG. 14, after step 2, the purification control method further includes a step 14.

In step 14, when the air conditioner indoor unit 20 operates in the first purification mode or the second purification mode, the air conditioner indoor unit 20 further operates in the heating mode.

A heating temperature may be in a range of 24° C. to 30° C., inclusive, and the temperature of the discharge terminal of the discharge device may be in a range of 30° C. to 60° C., inclusive. In this way, the generation of air positive ions and air negative ions may be promoted, and a room temperature may be adjusted to a comfortable temperature range of the human body, thereby reducing the adverse effects of the first purification mode or the second purification mode on the heating mode of the air conditioner indoor unit 20 and improving the comfort of room temperature.

For example, as shown in FIG. 1, when the air conditioner indoor unit 20 operates in the first purification mode or the second purification mode and operates in the heating mode simultaneously, the air conditioner 100 may control the heating temperature of the air conditioner indoor unit 20 by controlling an opening degree regulating valve of the compressor 301 and keep the purification apparatus 10 at a suitable temperature. Alternatively, the air conditioner 100 may control the temperature through a positive temperature coefficient (PTC) thermistor. In some embodiments, as shown in FIG. 3, the air conditioner indoor unit 20 includes a third control device 206. The third control device 206 is coupled to the terminal device and the electric control assembly 200 and configured to control whether the air conditioner indoor unit 20 operates in the first purification mode or the second purification mode. The terminal device is configured to remotely control the air conditioner indoor unit 20.

For example, the terminal device is a mobile device, and the mobile device is coupled to the third control device 206 in the air conditioner indoor unit 20 through an APP, so that the user may send a purification mode trigger instruction to the third control device 206 through the mobile device. In this way, the user may remotely control the air conditioner indoor unit 20.

Alternatively, the terminal device may be a remote controller, a wire controller, or a Bluetooth remote controller.

For example, the third control device 206 includes a processor. The processor may include a central processing unit (CPU), a microprocessor, or an application specific integrated circuit (ASIC) and may be configured to perform corresponding operations described with reference to the third control device 206 when the processor executes a program stored on a non-transitory computer readable media coupled to the third control device 206.

Figure 15:
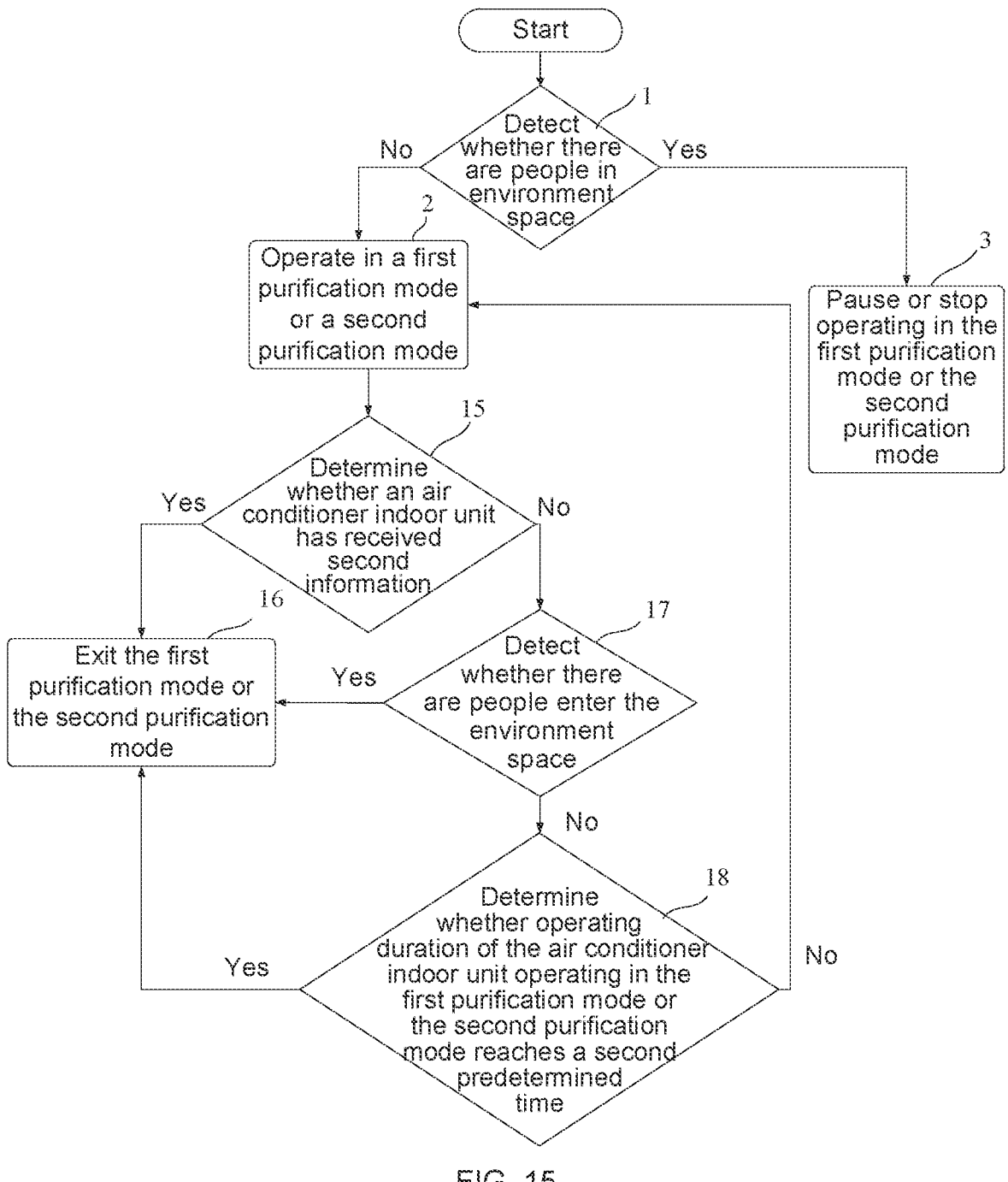
FIG. 15 is a flow diagram of yet another purification control method of an air conditioner indoor unit, in accordance with some embodiments.

FIG. 15 is a flow diagram of yet another purification control method of an air conditioner indoor unit, in accordance with some embodiments.

As shown in FIG. 15, after step 2, the purification control method further includes steps 15 to 18.

In step 15, it is determined whether the air conditioner indoor unit 20 has received second information. If so, step 16 is performed. If not, step 17 is performed.

For example, the second information is an instruction for exiting the first purification mode or the second purification mode sent by the user. In this way, it is beneficial for the user to control the operation mode of the air conditioner indoor unit 20.

In step 16, the air conditioner indoor unit 20 exits the first purification mode or the second purification mode.

In step 17, it is detected whether there are people entering the environment space. If so, step 16 is performed. If not, step 18 is performed.

In step 18, it is determined whether the operating duration of the air conditioner indoor unit 20 operating in the first purification mode or the second purification mode reaches a second predetermined time. If so, step 16 is performed. If not, step 2 is re-performed.

In the above steps, a third control device may feed the operation mode of the air conditioner indoor unit 20 back to the terminal device, and the user may view the operation mode of the air conditioner indoor unit 20 through the terminal device.

Some embodiments of the present disclosure provide a computer-readable storage medium (e.g., a non-transitory computer-readable storage medium). The computer-readable storage medium stores thereon computer program instructions that, when run on the second control device 4, cause the second control device 4 to perform the above purification control method of the air conditioner indoor unit.

For example, the computer-readable storage medium may include, but is not limited to a magnetic storage device (e.g., a hard disk, a floppy disk, or a magnetic tape), an optical disk (e.g., a compact disk (CD), a digital versatile disk (DVD)), a smart card, and a flash memory device (e.g., an erasable programmable read-only memory (EPROM), a card, a stick or a key drive). The various computer-readable storage media described in the embodiments of the present disclosure may represent one or more devices and/or other machine-readable storage media, which are used for storing information. The term "machine-readable storage medium" may include, but is not limited to, wireless channels and various other media capable of storing, containing, and/or carrying instruction(s) and/or data.

Some embodiments of the present disclosure provide a computer program product. The computer program product includes computer program instructions (for example, the computer program instructions stored on a non-transitory computer-readable storage medium). When the computer program instructions are executed by the computer, the computer program instructions cause the computer to perform the purification control method of the air conditioner indoor unit as described above.

Some embodiments of the present disclosure further provide a computer program. When the computer program is executed by a computer, the computer program causes the computer to perform the purification control method of the air conditioner indoor unit.

The foregoing descriptions are merely specific implementations of the present disclosure, but the protection scope of the present disclosure is not limited thereto. Changes or replacements that any person skilled in the art could conceive of within the technical scope of the present disclosure shall be included in the protection scope of the present disclosure. Therefore, the protection scope of the present disclosure shall be subject to the protection scope of the claims.

What is claimed is:

1. An air conditioner indoor unit, an operation mode of the air conditioner indoor unit including a first purification mode and a second purification mode, and the air conditioner indoor unit comprising:
    a power supply device;
    a control device;
    a negative electrode discharge device coupled to the power supply device and configured to discharge in the first purification mode or the second purification mode to ionize air to generate air negative ions; and
    a positive electrode discharge device coupled to the power supply device and configured to discharge in the first purification mode to ionize air to generate air positive ions; the air positive ions cooperating with the air negative ions generated by the negative electrode discharge device to perform disinfection and sterilization; wherein
    the control device is configured to:
        determine the operation mode of the air conditioner indoor unit according to first information;
        control the power supply device to supply power to the negative electrode discharge device and the positive electrode discharge device in a case where the operation mode of the air conditioner indoor unit is the first purification mode; and
        control the power supply device to supply power to the negative electrode discharge device and stop supplying power to the positive electrode discharge device in a case where the operation mode of the air conditioner indoor unit is the second purification mode; wherein
    the first information includes at least one of a purification mode trigger instruction, environment information, or operating duration information;
the negative electrode discharge device includes:
    a first pulse sub-circuit, the first pulse sub-circuit being coupled to the power supply device and configured to convert an input power signal to a first alternating current signal;
    a first voltage transformation sub-circuit, an input terminal of the first voltage transformation sub-circuit being coupled to an output terminal of the first pulse sub-circuit, and the first voltage transformation sub-circuit being configured to transform a voltage of the first alternating current signal and output a first voltage-transformed signal;
    a first voltage multiplying sub-circuit, an input terminal of the first voltage multiplying sub-circuit being coupled to an output terminal of the first voltage transformation sub-circuit, and the first voltage multiplying sub-circuit being configured to multiply a voltage of the first voltage-transformed signal and output a first voltage-multiplied signal; and
    a negative discharge electrode, the negative discharge electrode being coupled to an output terminal of the first voltage multiplying sub-circuit and configured to discharge due to excitation of the first voltage-multiplied signal to make surrounding air generate the air negative ions; and
the positive electrode discharge device includes:
    a second pulse sub-circuit, the second pulse sub-circuit being coupled to the power supply device through the control device and configured to convert an input power signal to a second alternating current signal;
    a second voltage transformation sub-circuit, an input terminal of the second voltage transformation sub-circuit being coupled to an output terminal of the second pulse sub-circuit, and the second voltage transformation sub-circuit being configured to transform a voltage of the second alternating current signal and output a second voltage-transformed signal;
    a second voltage multiplying sub-circuit, an input terminal of the second voltage multiplying sub-circuit being coupled to an output terminal of the second voltage transformation sub-circuit, and the second voltage multiplying sub-circuit being configured to multiply a voltage of the second voltage-transformed signal and output a second voltage-multiplied signal; and
    a positive discharge electrode, the positive discharge electrode being coupled to an output terminal of the second voltage multiplying sub-circuit and configured to discharge due to excitation of the second voltage-multiplied signal to make the surrounding air generate the air positive ions.

2. The air conditioner indoor unit according to claim 1, wherein the air conditioner indoor unit satisfies at least one of:
    that the air conditioner indoor unit is further configured to receive the purification mode trigger instruction; and the control device is further configured to determine the operation mode of the air conditioner indoor unit according to the purification mode trigger instruction;

that the control device includes a sensing assembly configured to collect the environment information; and the control device is further configured to determine the operation mode of the air conditioner indoor unit according to the environment information collected by the sensing assembly;

or that the control device is further configured to determine the operation mode of the air conditioner indoor unit according to the operating duration information; the operating duration information includes operating duration information of the air conditioner indoor unit, and the operating duration information of the air conditioner indoor unit operating in the first purification mode or operating duration information of the air conditioner indoor unit operating in the second purification mode.

3. The air conditioner indoor unit according to claim 2, wherein the environment information includes at least one of temperature information, wind speed information, light information, or sound information; and the control device is further configured to determine that the operation mode of the air conditioner indoor unit is the first purification mode or the second purification mode in a case where at least one of the temperature information, the wind speed information, the light information, or the sound information collected by the sensing assembly reaches a corresponding preset threshold.

4. The air conditioner indoor unit according to claim 1, wherein the control device includes a control assembly and a switch assembly, and the control assembly is coupled to a control terminal of the switch assembly;

the control assembly is configured to:

control the switch assembly to be turned on in a case where the operation mode of the air conditioner indoor unit is the first purification mode; and control the switch assembly to be turned off in a case where the operation mode of the air conditioner indoor unit is the second purification mode.

5. The air conditioner indoor unit according to claim 4, wherein a first input terminal of the negative electrode discharge device is coupled to a positive terminal of the power supply device, and a second input terminal of the negative electrode discharge device is coupled to a negative terminal of the power supply device;

a first input terminal of the positive electrode discharge device is coupled to the positive terminal of the power supply device, and a second input terminal of the positive electrode discharge device is coupled to a first terminal of the switch assembly; and a second terminal of the switch assembly is coupled to the negative terminal of the power supply device.

6. The air conditioner indoor unit according to claim 5, wherein the control device further includes:

a resistor assembly, a first terminal of the resistor assembly being coupled to the control assembly; and a capacitor assembly, a first terminal of the capacitor assembly being coupled to a second terminal of the resistor assembly, and a second terminal of the capacitor assembly being coupled to the negative terminal of the power supply device.

7. The air conditioner indoor unit according to claim 4, wherein the control assembly is further configured to determine whether the operation mode of the air conditioner indoor unit is the first purification mode or the second purification mode according to the purification mode trigger instruction or the operating duration information.

8. The air conditioner indoor unit according to claim 4, wherein a first input terminal of the negative electrode discharge device is coupled to a positive terminal of the power supply device, and a second input terminal of the negative electrode discharge device is coupled to a negative terminal of the power supply device;

a first input terminal of the positive electrode discharge device is coupled to a first terminal of the switch assembly, and a second input terminal of the positive electrode discharge device is coupled to a second terminal of the switch assembly; and a third terminal of the switch assembly is coupled to a positive terminal of the power supply device, and a fourth terminal of the switch assembly is coupled to a negative terminal of the power supply device.

9. The air conditioner indoor unit according to claim 1, wherein the power supply device includes a first power supply and a second power supply;

a first input terminal of the negative electrode discharge device is coupled to a positive terminal of the first power supply, and a second input terminal of the negative electrode discharge device is coupled to a first terminal of the control device;

a first input terminal of the positive electrode discharge device is coupled to a positive terminal of the second power supply, and a second input terminal of the positive electrode discharge device is coupled to a second terminal of the control device; and a third terminal of the control device is coupled to negative terminals of the first power supply and the second power supply.

10. The air conditioner indoor unit according to claim 9, wherein the control device is further configured to:

control the first power supply to supply power to the negative electrode discharge device and control the second power supply to supply power to the positive electrode discharge device in a case where the operation mode of the air conditioner indoor unit is the first purification mode; and control the first power supply to supply power to the negative electrode discharge device and control the second power supply to stop supplying power to the positive electrode discharge device in a case where the operation mode of the air conditioner indoor unit is the second purification mode.

11. The air conditioner indoor unit according to claim 1, further comprising a human body detection device and an electric control assembly, wherein the human body detection device is coupled to the electric control assembly and configured to detect whether there are people in environment space; and the electric control assembly is coupled to the power supply device and configured to:

control the power supply device to be turned on in response to the human body detection device detecting that there are no people in the environment space, so that the air conditioner indoor unit operates in the first purification mode or the second purification mode; and control the power supply device to be turned off in response to the human body detection device detecting that there are people in the environment space, so that the air conditioner indoor unit pauses or stops operating in the first purification mode or the second purification mode.

12. The air conditioner indoor unit according to claim 11, wherein the operation mode of the air conditioner indoor unit further includes a heating mode; and the air conditioner indoor unit is configured to operate in the heating mode when the air conditioner indoor unit operates in the first purification mode or the second purification mode, and a heating temperature is any value in a range from 24° C. to 30° C., inclusive.

13. The air conditioner indoor unit according to claim 11, further comprising an air outlet guide plate, an indoor heat exchanger, and an indoor fan; the air outlet guide plate, the indoor heat exchanger, and the indoor fan being coupled to the electric control assembly, wherein in a case where the air conditioner indoor unit operates in the first purification mode or the second purification mode, the air outlet guide plate is in a fully open state, and a temperature of the indoor heat exchanger is less than or equal to a predetermined temperature, the electric control assembly is further configured to control the indoor fan to operate at a first wind speed for a first predetermined time.

14. The air conditioner indoor unit according to claim 13, wherein the electric control assembly is further configured to control the indoor fan to operate at a second wind speed after the indoor fan operates at the first wind speed for the first predetermined time, the second wind speed being greater than the first wind speed; or the electric control assembly is further configured to control the indoor fan to operate at the second wind speed in a case where the air conditioner indoor unit operates in the first purification mode or the second purification mode, the air outlet guide plate is in the fully open state, and the temperature of the indoor heat exchanger is greater than the predetermined temperature, the second wind speed being greater than the first wind speed.

15. The air conditioner indoor unit according to claim 1, further comprising an air outlet, wherein the negative electrode discharge device includes a negative discharge electrode; and the positive electrode discharge device includes a positive discharge electrode, the negative discharge electrode and the positive discharge electrode are disposed at the air outlet and coupled to the control device.

16. The air conditioner indoor unit according to claim 15, wherein when the air conditioner indoor unit operates in the first purification mode, the control device is further configured to control a temperature of a discharge terminal of the positive discharge electrode to be any value in a range from 30° C. to 60° C., and control a temperature of a discharge terminal of the negative discharge electrode to be any value in a range 30° C. to 60° C.; and when the air conditioner indoor unit operates in the second purification mode, the control device is further configured to control the temperature of the discharge terminal of the negative discharge electrode to be any value in the range 30° C. to 60° C.

17. An air conditioner, comprising:

the air conditioner indoor unit according to claim 1; and an air conditioner outdoor unit connected with the air conditioner indoor unit.

18. A purification control method of an air conditioner indoor unit, an operation mode of the air conditioner indoor unit including a first purification mode and a second purification mode, and the air conditioner indoor unit including a positive electrode discharge device and a negative electrode discharge device; when the air conditioner indoor unit operates in the first purification mode, the positive electrode discharge device and the negative electrode discharge device operating; and when the air conditioner indoor unit operates in the second purification mode, the negative electrode discharge device operating;

the purification control method comprising:

detecting, by the air conditioner indoor unit, whether there are people in environment space;

operating, by the air conditioner indoor unit, in the first purification mode or the second purification mode when detecting there are no people in the environment space; and pausing or stopping operating, by the air conditioner indoor unit, in the first purification mode or the second purification mode when detecting there are people in the environment space;

wherein the negative electrode discharge device includes:

a first pulse sub-circuit, the first pulse sub-circuit being coupled to the power supply device and configured to convert an input power signal to a first alternating current signal;

a first voltage transformation sub-circuit, an input terminal of the first voltage transformation sub-circuit being coupled to an output terminal of the first pulse sub-circuit, and the first voltage transformation sub-circuit being configured to transform a voltage of the first alternating current signal and output a first voltage-transformed signal;

a first voltage multiplying sub-circuit, an input terminal of the first voltage multiplying sub-circuit being coupled to an output terminal of the first voltage transformation sub-circuit, and the first voltage multiplying sub-circuit being configured to multiply a voltage of the first voltage-transformed signal and output a first voltage-multiplied signal; and a negative discharge electrode, the negative discharge electrode being coupled to an output terminal of the first voltage multiplying sub-circuit and configured to discharge due to excitation of the first voltage-multiplied signal to make surrounding air generate the air negative ions; and the positive electrode discharge device includes:

a second pulse sub-circuit, the second pulse sub-circuit being coupled to the power supply device through the control device and configured to convert an input power signal to a second alternating current signal;

a second voltage transformation sub-circuit, an input terminal of the second voltage transformation sub-circuit being coupled to an output terminal of the second pulse sub-circuit, and the second voltage transformation sub-circuit being configured to transform a voltage of the second alternating current signal and output a second voltage-transformed signal;

a second voltage multiplying sub-circuit, an input terminal of the second voltage multiplying sub-circuit being coupled to an output terminal of the second voltage transformation sub-circuit, and the second voltage multiplying sub-circuit being configured to multiply a voltage of the second voltage-transformed signal and output a second voltage-multiplied signal; and a positive discharge electrode, the positive discharge electrode being coupled to an output terminal of the second voltage multiplying sub-circuit and configured to discharge due to excitation of the second voltage-multiplied signal to make the surrounding air generate the air positive ions.

19. The purification control method according to claim 18, wherein the operation mode of the air conditioner indoor unit further includes a heating mode;

the purification control method further comprises that:

the air conditioner indoor unit operates in the heating mode when the air conditioner indoor unit operates in the first purification mode or the second purification mode; wherein a heating temperature of the heating mode is any value in a range from 24° C. to 30° C.

\* \* \* \* \*